United States Patent [19]

Nohira et al.

[11] Patent Number: 5,217,644
[45] Date of Patent: Jun. 8, 1993

[54] MESOMORPHIC COMPOUND, LIQUID CRYSTAL COMPOSITION CONTAINING SAME, LIQUID CRYSTAL DEVICE USING SAME AND DISPLAY APPARATUS

[75] Inventors: Hiroyuki Nohira, Urawa; Yoko Yamada; Shinichi Nakamura, both of Atsugi; Akira Sakaigawa, Urawa; Yasumasa Tashiro, Tokorozawa; Yoshio Aoki, Urawa, all of Japan

[73] Assignee: Canon Kabushiki Kaisha, Tokyo, Japan

[21] Appl. No.: 647,362

[22] Filed: Jan. 29, 1991

[30] Foreign Application Priority Data

Jan. 29, 1990 [JP] Japan .................................. 2-015976

[51] Int. Cl.$^5$ .................... C09K 19/06; C09K 19/34; C09K 19/32; G02F 1/13
[52] U.S. Cl. .................... 252/299.6; 252/299.61; 252/299.62; 252/299.63; 252/299.66; 252/299.67; 252/299.01; 544/298; 560/65; 560/102; 568/647; 359/103; 546/339
[58] Field of Search .................... 252/299.61, 299.66, 252/299.67, 299.63, 299.62, 299.01; 544/298; 546/339; 560/102, 65; 568/647; 359/103

[56] References Cited

U.S. PATENT DOCUMENTS

| | | | |
|---|---|---|---|
| 4,367,924 | 1/1983 | Clark et al. | 350/334 |
| 4,917,817 | 4/1990 | Nohira et al. | 252/299.01 |
| 4,918,213 | 4/1990 | Nohira et al. | 558/271 |
| 4,921,632 | 5/1990 | Nakamura et al. | 252/299.1 |
| 4,973,738 | 11/1990 | Suzuki et al. | |
| 5,098,600 | 3/1992 | Nakamura et al. | 252/299.61 |

FOREIGN PATENT DOCUMENTS

| | | |
|---|---|---|
| 0294852 | 12/1988 | European Pat. Off. . |
| 0301511 | 2/1989 | European Pat. Off. . |
| 0325228 | 7/1989 | European Pat. Off. . |
| 0327349 | 8/1989 | European Pat. Off. . |
| 0330491 | 8/1989 | European Pat. Off. . |
| 0335348 | 10/1989 | European Pat. Off. . |
| 107216 | 8/1981 | Japan . |

OTHER PUBLICATIONS

Applied Physics Letters, vol. 18, No. 4 (1971) 127.8.

*Primary Examiner*—Robert L. Stoll
*Assistant Examiner*—C. Harris
*Attorney, Agent, or Firm*—Fitzpatrick, Cella, Harper & Scinto

[57] ABSTRACT

A mesomorphic compound represented by the following formula (I):

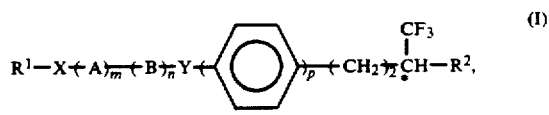

wherein $R^1$ denotes an alkyl group having 1–18 carbon atoms; $R^2$ denotes an alkyl group having 1–12 carbon atoms; A and B respectively denote

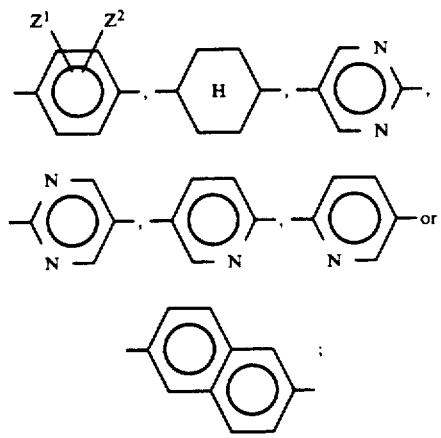

$Z^1$ and $Z^2$ respectively denote —H, 'CH$_3$, —OCH$_3$, —CN or halogen; m and n respectively denote 0, 1 or 2 and p denotes 1 or 2 with proviso that m+n+p =2 or 3; X denotes a single bond, (Abstract continued on next page.)

$-O-$, $-\underset{\underset{O}{\|}}{C}O-$, $-O\underset{\underset{O}{\|}}{C}-$, $-\underset{\underset{O}{\|}}{C}-$ or $-O\underset{\underset{O}{\|}}{C}O-$;

Y denotes a single bond $-\underset{\underset{O}{\|}}{C}O-$, $-O\underset{\underset{O}{\|}}{C}-$, $-CH_2O-$, $-OCH_2-$, $-\underset{\underset{O}{\|}}{C}CH_2-$ or $-CH_2\underset{\underset{O}{\|}}{C}-$; and $\overset{*}{C}$ denotes an asymmetric carbon atom.

15 Claims, 4 Drawing Sheets

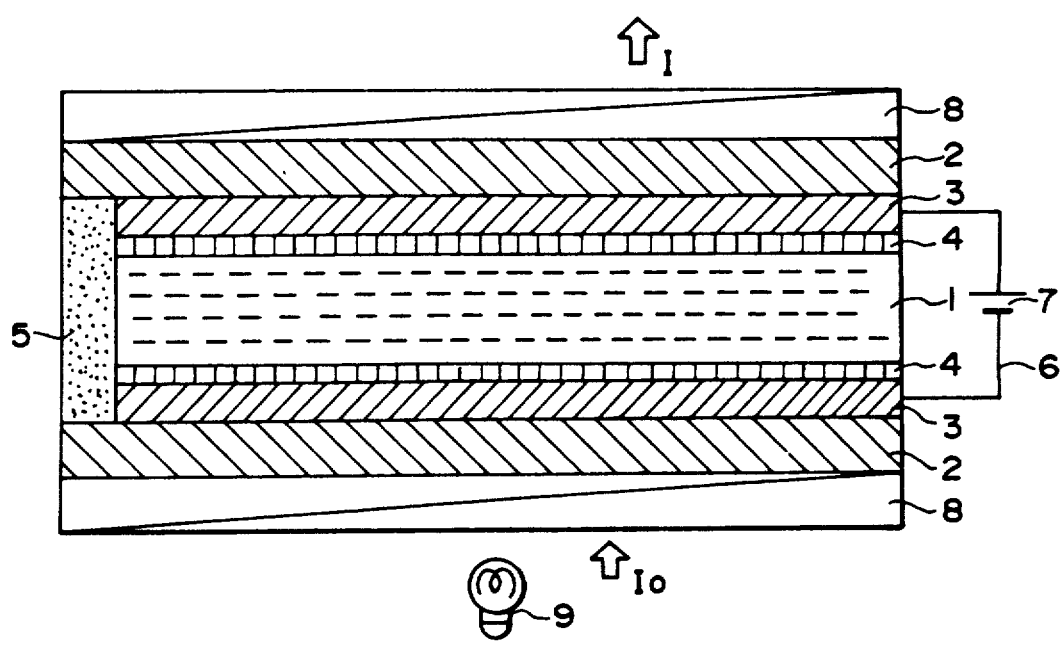
F I G. 1

MESOMORPHIC COMPOUND, LIQUID CRYSTAL COMPOSITION CONTAINING SAME, LIQUID CRYSTAL DEVICE USING SAME AND DISPLAY APPARATUS

FIELD OF THE INVENTION AND RELATED ART

The present invention relates to a novel mesomorphic compound, a liquid crystal composition containing the compound, a liquid crystal device using the composition and a display apparatus, and more particularly to a novel liquid crystal composition with improved responsiveness to an electric field and a liquid crystal device using the liquid crystal composition for use in a liquid crystal display apparatus, a liquid crystal-optical shutter, etc.

Hitherto, liquid crystal devices have been used as an electro-optical device in various fields. Most liquid crystal devices which have been put into practice use TN (twisted nematic) type liquid crystals, as shown in "Voltage-Dependent Optical Activity of a Twisted Nematic Liquid Crystal" by M. Schadt and W. Helfrich "Applied Physics Letters" Vol. 18, No. 4 (Feb. 15, 1971) pp. 127-128.

These devices are based on the dielectric alignment effect of a liquid crystal and utilize an effect that the average molecular axis direction is directed to a specific direction in response to an applied electric field because of the dielectric anisotropy of liquid crystal molecules. It is said that the limit of response speed is on the order of milli-seconds, which is too slow for many uses. On the other hand, a simple matrix system of driving is most promising for application to a large-area flat display in view of cost, productivity, etc., in combination. In the simple matrix system, an electrode arrangement wherein scanning electrodes and signal electrodes are arranged in a matrix, and for driving, a multiplex driving scheme is adopted wherein an address signal is sequentially, periodically and selectively applied to the scanning electrodes and prescribed data signals are selectively applied in parallel to the signal electrodes in synchronism with the address signal.

When the above-mentioned TN-type liquid crystal is used in a device of such a driving system, a certain electric field is applied to regions where a scanning electrode is selected and signal electrodes are not selected or regions where a scanning electrode is not selected and a signal electrode is selected (which regions are so called "half-selected points"). If the difference between a voltage applied to the selected points and a voltage applied to the half-selected points is sufficiently large, and a voltage threshold level required for allowing liquid crystal molecules to be aligned or oriented perpendicular to an electric field is set to a value therebetween, display devices normally operate. However, in fact, as the number (N) of scanning lines increases, a time (duty ratio) during which an effective electric field is applied to one selected point when a whole image area (corresponding to one frame) is scanned decreases with a ratio of 1/N. Accordingly, the larger the number of scanning lines are, the smaller is the voltage difference of an effective value applied to a selected point and non-selected points when scanning is repeatedly effected. As a result, this leads to unavoidable drawbacks of lowering of image contrast or occurrence of interference or crosstalk. These phenomena are regarded as essentially unavoidable problems appearing when a liquid crystal having no bistability (i.e. liquid crystal molecules are horizontally oriented with respect to the electrode surface as stable state and is vertically oriented with respect to the electrode surface only when an electric field is effectively applied) is driven (i.e. repeatedly scanned) by making use of a time storage effect. To overcome these drawbacks, the voltage averaging method, the two-frequency driving method, the multiple matrix method, etc. has been already proposed. However, any method is not sufficient to overcome the above-mentioned drawbacks. As a result, it is the present state that the development of large image area or high packaging density in respect to display elements is delayed because it is difficult to sufficiently increase the number of scanning lines.

To overcome drawbacks with such prior art liquid crystal devices, the use of liquid crystal devices having bistability has been proposed by Clark and Lagerwall (e.g. Japanese Laid-Open Patent Appln. No. 56-107216, U.S. Pat. No. 4,367,924, etc.). In this instance, as the liquid crystals having bistability, ferroelectric liquid crystals having chiral smectic C-phase (SmC*) or H-phase (SmH*) are generally used. These liquid crystals have bistable states of first and second stable states with respect to an electric field applied thereto. Accordingly, as different from optical modulation devices in which the above-mentioned TN-type liquid crystals are used, the bistable liquid crystal molecules are oriented to first and second optically stable states with respect to one and the other-electric field vectors, respectively. Further, this type of liquid crystal has a property (bistability) of assuming either one of the two stable states in response to an applied electric and retaining the resultant state in the absence of an electric field.

In addition to the above-described characteristic of showing bistability, such a ferroelectric liquid crystal (hereinafter sometimes abbreviated as "FLC") has an excellent property, i.e., a high-speed responsiveness. This is because the spontaneous polarization of the ferroelectric liquid crystal and an applied electric field directly interact with each other to induce transition of orientation states. The resultant response speed is faster than the response speed due to the interaction between dielectric anisotropy and an electric field by 3 to 4 digits.

Thus, a ferroelectric liquid crystal potentially has very excellent characteristics, and by making use of these properties, it is possible to provide essential improvements to many of the above-mentioned problems with the conventional TN-type devices. Particularly, the application to a high-speed optical shutter and a display of a high density and a large picture is expected. For this reason, there has been made extensive research with respect to liquid crystal materials showing ferroelectricity. However, ferroelectric liquid crystal materials developed heretofore cannot be said t satisfy sufficient characteristics required for a liquid crystal device including low-temperature operation characteristic, high-speed responsiveness, etc. Among a response time $\tau$, the magnitude of spontaneous polarization Ps and viscosity $\eta$, the following relationship exists: $\tau=\eta/(Ps\cdot E)$, where E is an applied voltage. Accordingly, a high response speed can be obtained by (a) increasing the spontaneous polarization Ps, (b) lowering the viscosity $\eta$, or (c) increasing the applied voltage E. However, the driving voltage has a certain upper limit in view of driving with IC, etc., and should desirably be as low as possible. Accordingly, it is actually necessary to lower the viscosity or increase the spontaneous polarization A ferroelectric chiral smectic liquid crystal having a large spontaneous polarization generally provides a large internal electric field in a cell given by the spontaneous polarization and is liable to pose many constraints on the device construction giving bistability. Further, an excessively large spontaneous polarization is liable to accompany an increase in viscosity, so that remarkable increase in response speed may not be attained as a result.

Further, if it is assumed that the operation temperature of an actual display device is 5°-40° C., the response speed changes by a factor of about 20, so that it actually exceeds the range controllable by driving voltage and frequency.

As described hereinabove, commercialization of a ferroelectric liquid crystal device requires a liquid crystal composition assuming a chiral smectic phase which has not only a large spontaneous polarization but also a low viscosity, a high-speed responsiveness and a small temperature-dependence of response speed.

SUMMARY OF THE INVENTION

An object of the present invention is to provide a mesomorphic compound, a liquid crystal composition, particularly a chiral smectic liquid crystal composition, containing the mesomorphic compound for providing a practical ferroelectric liquid crystal device, a liquid crystal device using the liquid crystal composition and having a high response speed and a smaller temperature-dependence of the response speed, and a display apparatus.

According to the present invention, there is provided a mesomorphic compound represented by the following formula (I):

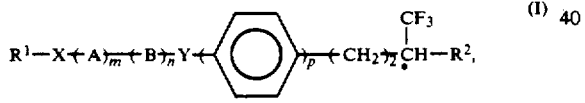

wherein $R^1$ denotes an alkyl group having 1-18 carbon atoms; $R^2$ denotes an alkyl group having 1-12 carbon atoms; A and B respectively denote

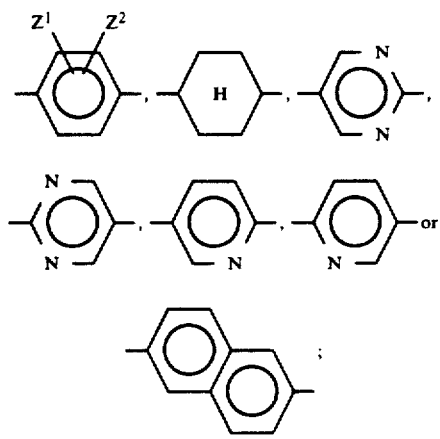

$Z^1$ and $Z^2$ respectively denote —H, —CH$_3$, —OCH$_3$, —CN or halogen; m and n respectively denote 0, 1 or 2 and p denotes 1 or 2 with proviso that $m+n+p=2$ or 3; X denotes a single bond,

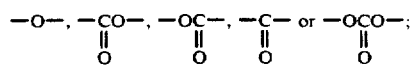

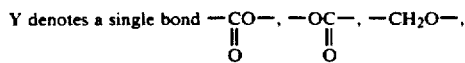

denotes an asymmetric carbon atom.

According to the present invention, there is further provided a liquid crystal composition containing at least one species of the mesomorphic compound as described above.

The present invention further provides a liquid crystal device comprising a pair of substrates and such a liquid crystal composition as described above disposed between the electrode plates, and a display apparatus comprising the liquid crystal device.

These and other objects, features and advantages of the present invention will become more apparent upon a consideration of the following description of the preferred embodiments of the present invention taken in conjunction with the accompanying drawings.

BRIEF DESCRIPTION OF THE DRAWINGS

FIG. 1 is a schematic sectional view of a liquid crystal display device using a liquid crystal composition assuming a chiral smectic phase;

DETAILED DESCRIPTION OF THE INVENTION

Figure 2:
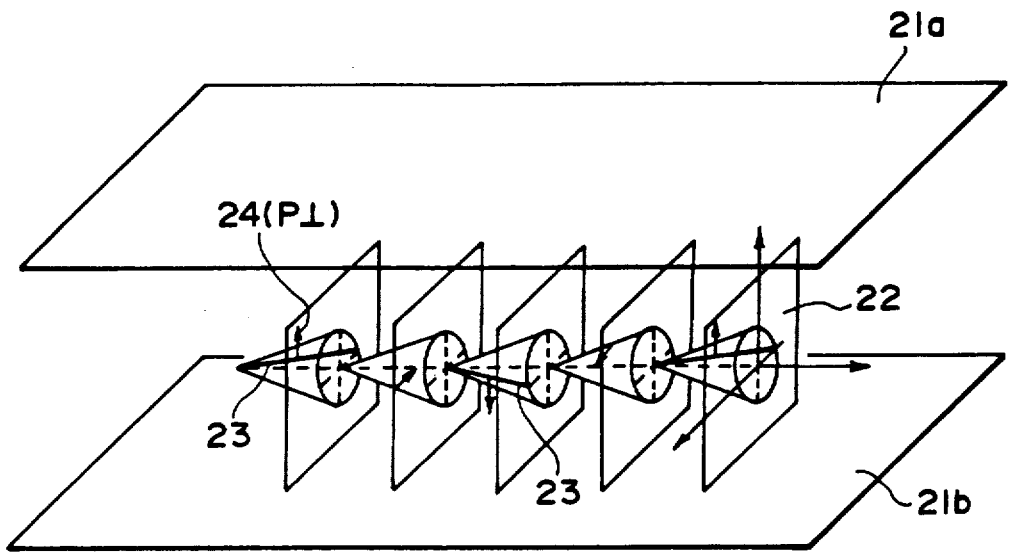
FIGS. 2 and 3 are schematic perspective views of a device cell embodiment for illustrating the operation principle of a liquid crystal device utilizing ferroelectricity of a liquid crystal composition.

In the formula (I) as described above, preferred examples of $R^1$ may include a linear or branched alkyl group having 2-16 carbon atoms. Preferred examples of $R^2$ may include a linear or branched alkyl group having 2-10 carbon atoms.

Particularly, preferred examples of the mesomorphic compound of the formula (I) may include the following formulas (a)-(z):

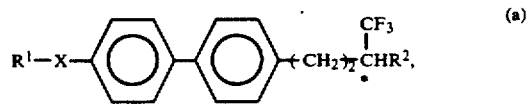

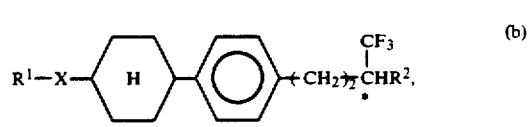

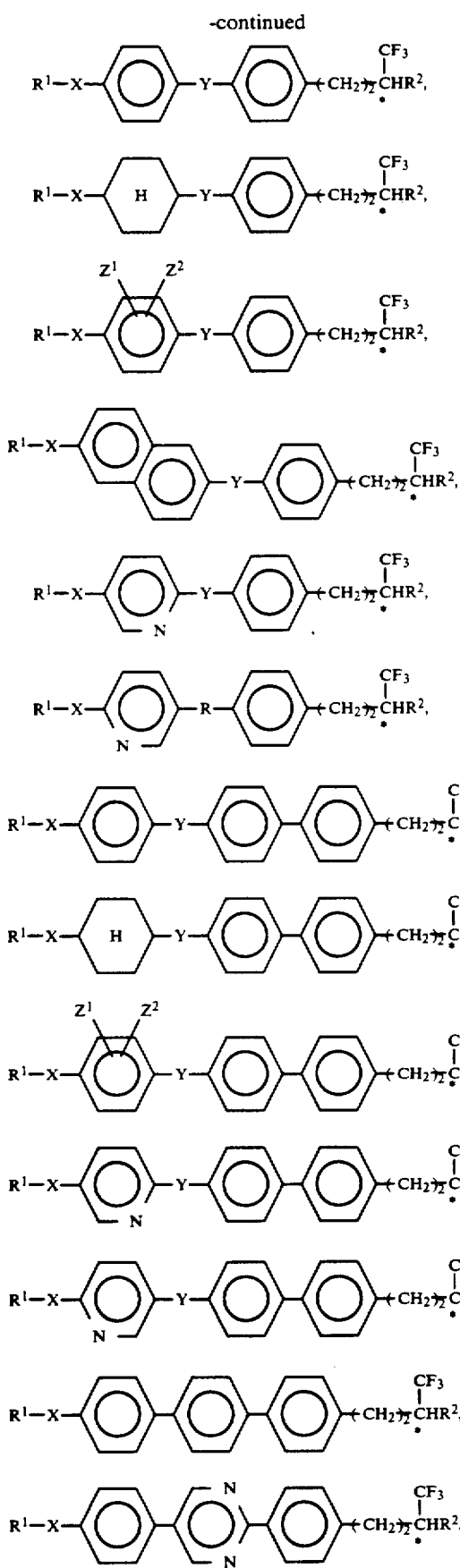
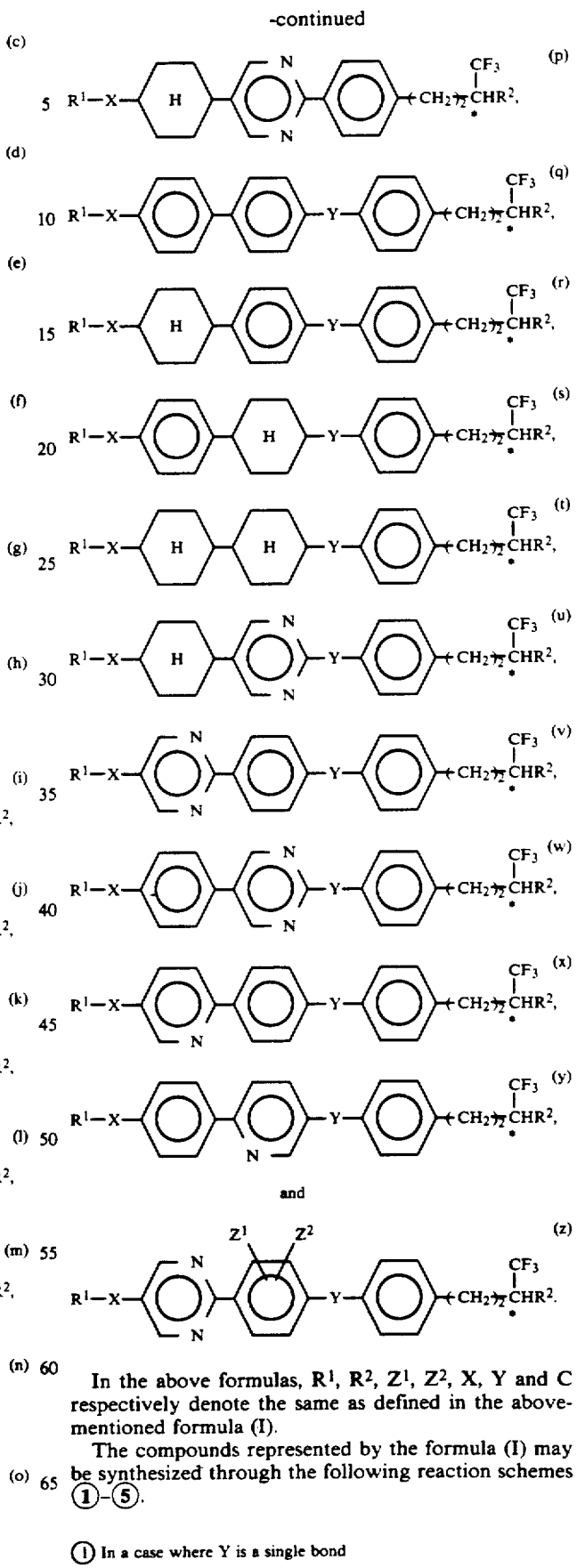
In the above formulas, $R^1$, $R^2$, $Z^1$, $Z^2$, X, Y and C respectively denote the same as defined in the above-mentioned formula (I).
The compounds represented by the formula (I) may be synthesized through the following reaction schemes ①–⑤.
① In a case where Y is a single bond 5,217,644
-continued
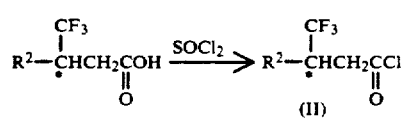
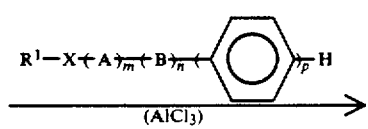
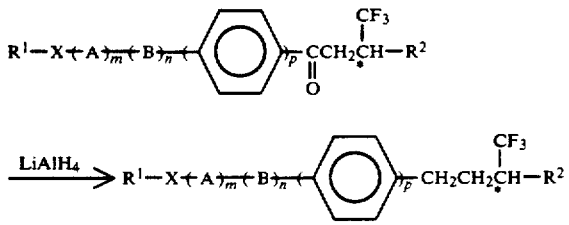
② In a case where Y is —CO— or —CH₂O—
                        ‖
                        O
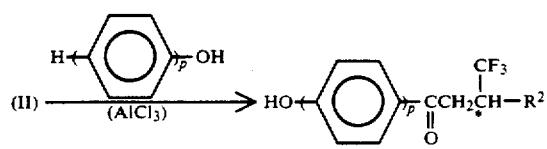
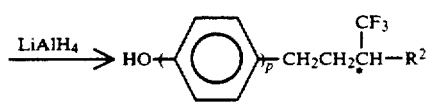
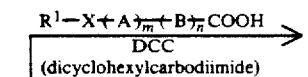
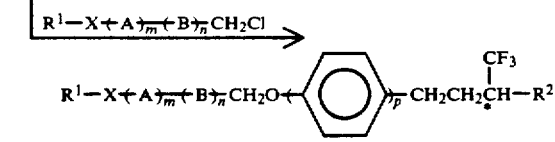
③ In a case where Y is —OC— or —OCH₂—
                        ‖
                        O
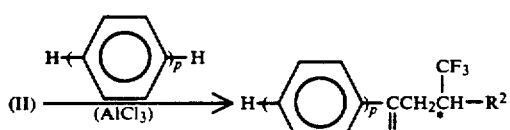
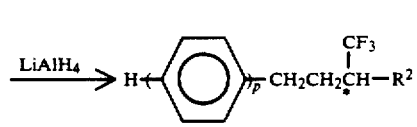
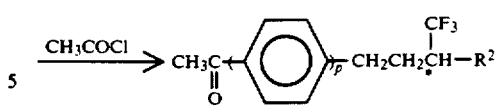
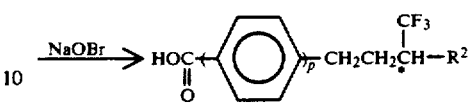
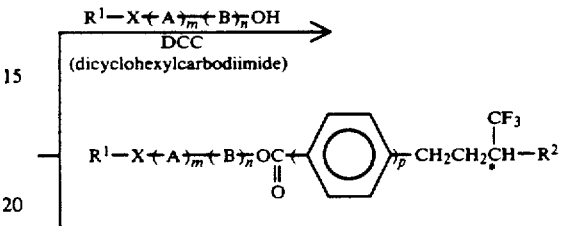
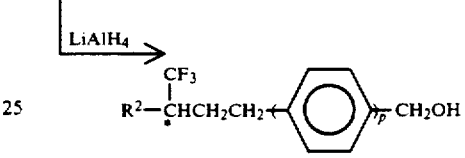
④ In a case where Y is —CCH₂—
                       ‖
                       O
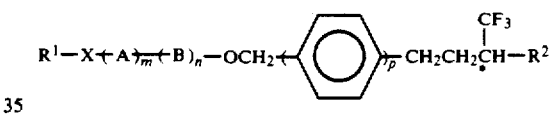
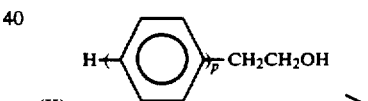
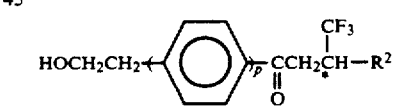
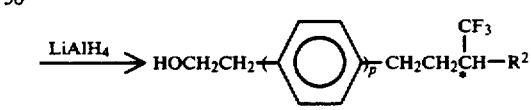
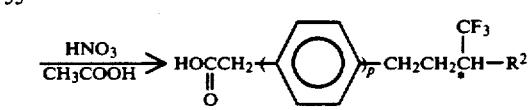
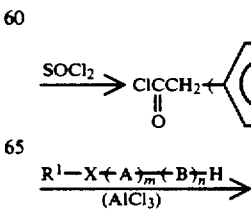

-continued

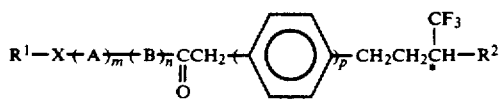

⑤ In a case where Y is —CH₂C—
                              ‖
                              O

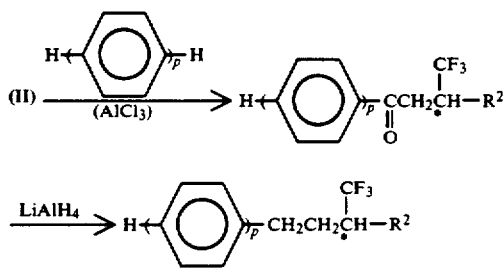

-continued

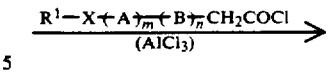

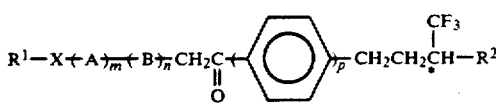

In the above, $R^1$, $R^2$, X, A, B, m, n and p respectively denote the same as defined above.

The mesomorphic compound of the formula (I) is optically active and may be applied to a liquid crystal device utilizing ferroelectrically when the mesomorphic compound assumes a chiral smectic phase by itself.

Specific examples of the mesomorphic compounds represented by the above-mentioned general formula (I) may include those shown by the following structural formulas.

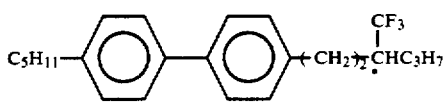
(I-1)

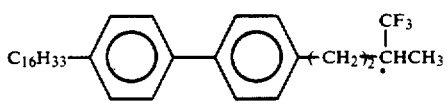
(I-2)

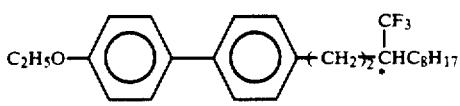
(I-3)

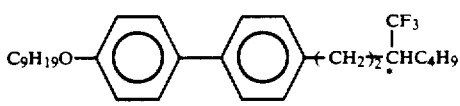
(I-4)

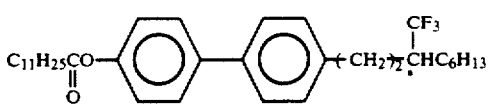
(I-5)

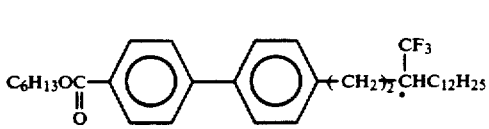
(I-6)

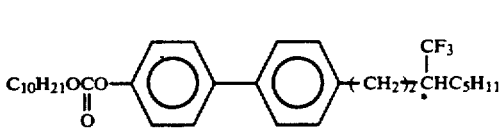
(I-7)

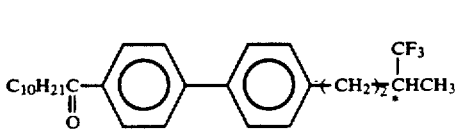
(I-8)

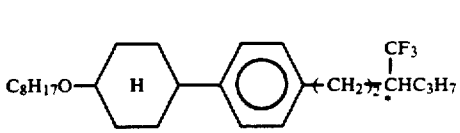
(I-9)

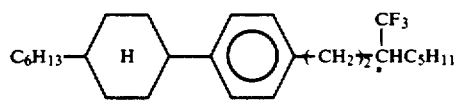 (I-10)
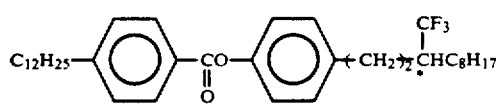 (I-11)
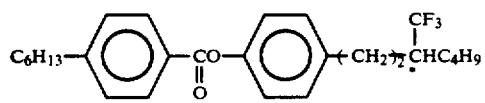 (I-12)
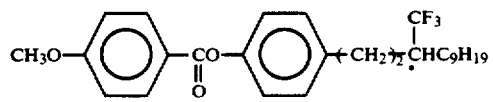 (I-13)
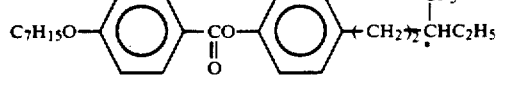 (I-14)
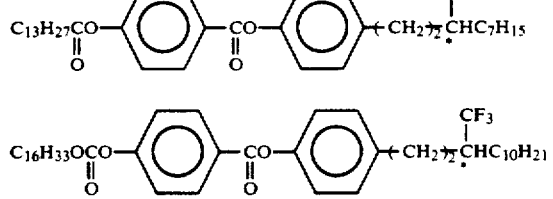 (I-15)
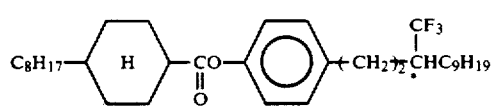 (I-16)
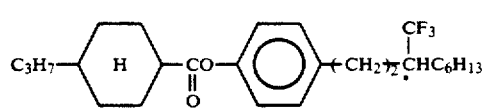 (I-17)
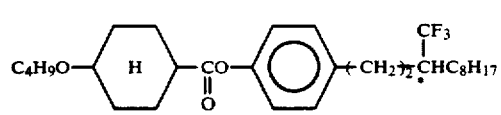 (I-18)
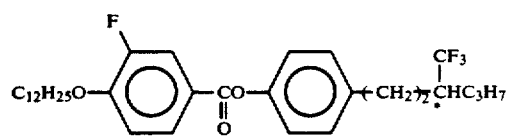 (I-19)
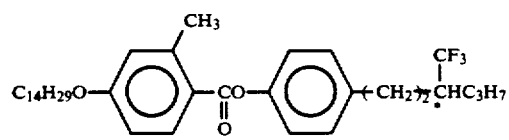 (I-20)
(I-21)
(I-22)
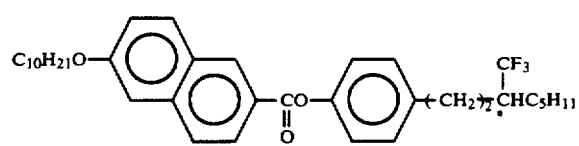

-continued
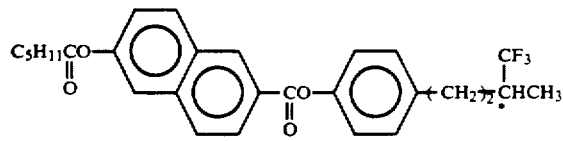 (I-23)
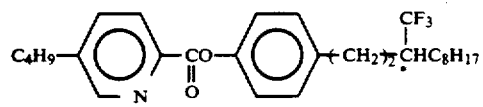 (I-24)
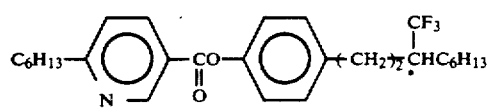 (I-25)
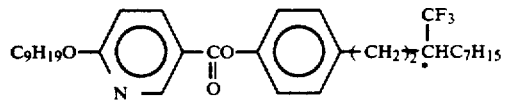 (I-26)
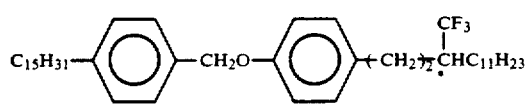 (I-27)
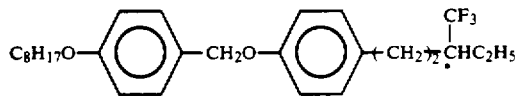 (I-28)
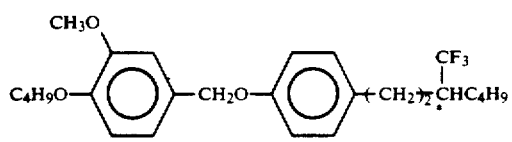 (I-29)
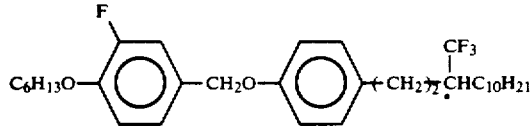 (I-30)
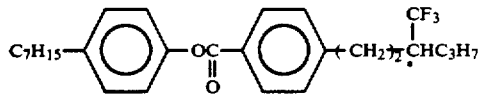 (I-31)
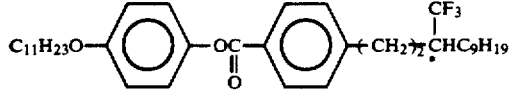 (I-32)
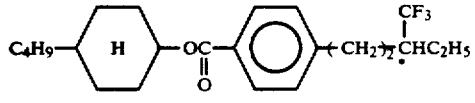 (I-33)
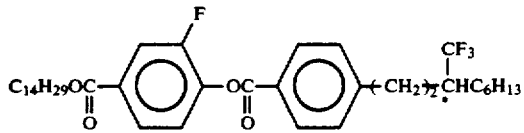 (I-34)

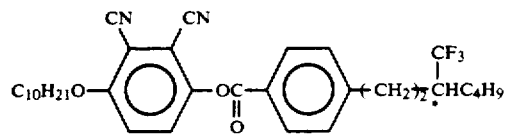
(I-35)
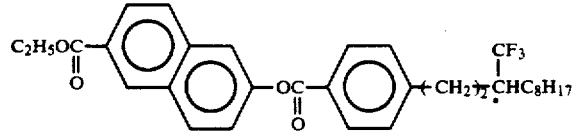
(I-36)
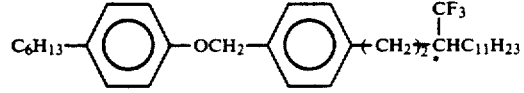
(I-37)
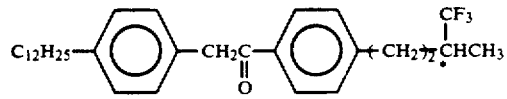
(I-38)
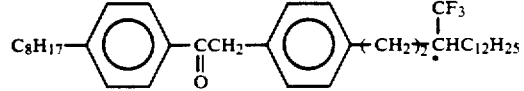
(I-39)
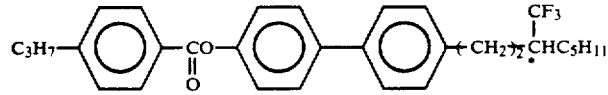
(I-40)
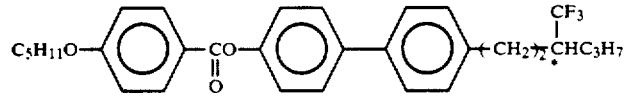
(I-41)
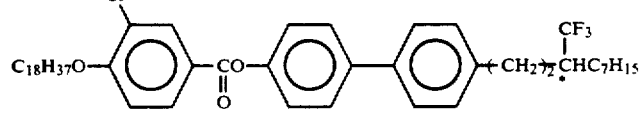
(I-42)
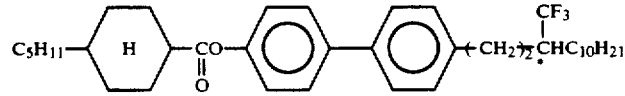
(I-43)
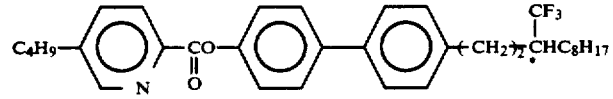
(I-44)
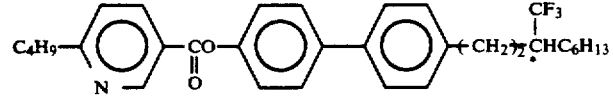
(I-45)
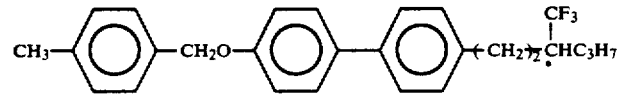
(I-46)
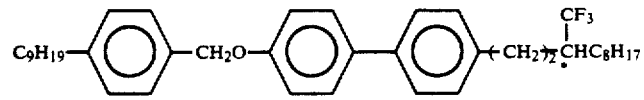
(I-47)

-continued
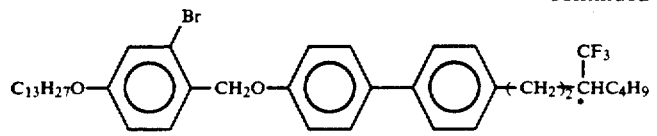
(I-48)
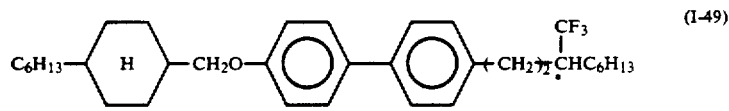
(I-49)
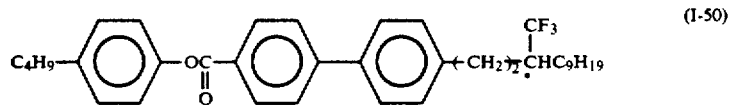
(I-50)
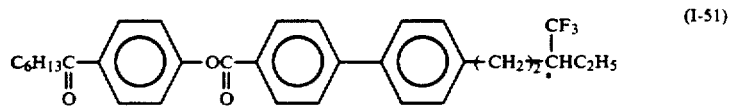
(I-51)
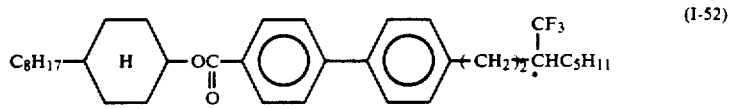
(I-52)
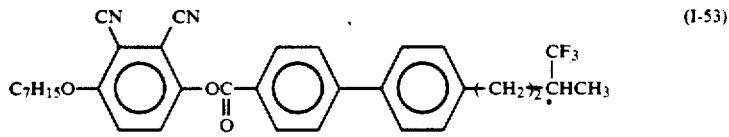
(I-53)
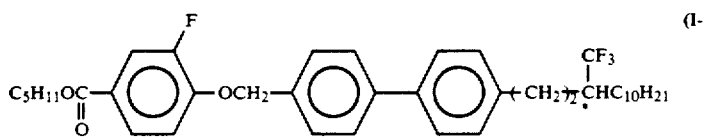
(I-54)
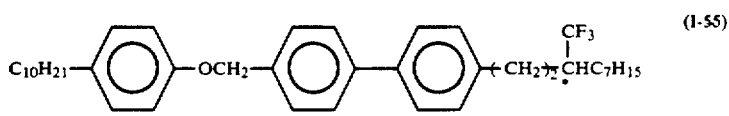
(I-55)
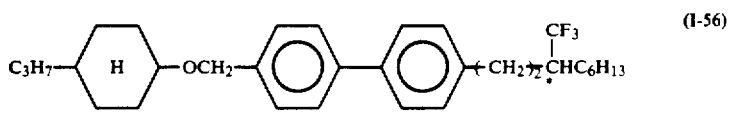
(I-56)
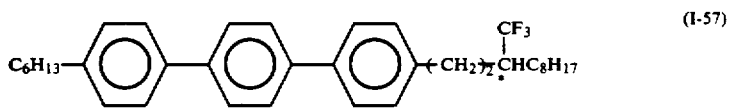
(I-57)
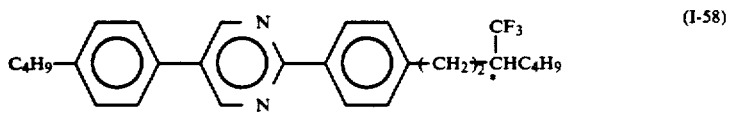
(I-58)
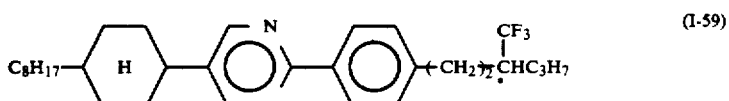
(I-59)
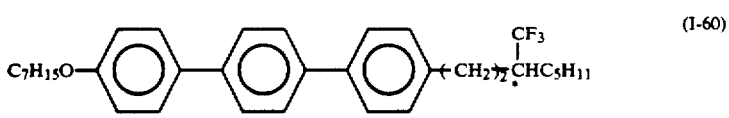
(I-60)

-continued
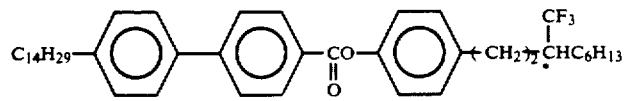 (I-61)
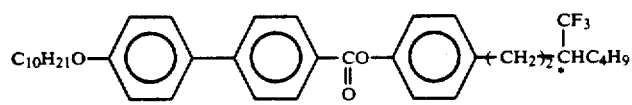 (I-62)
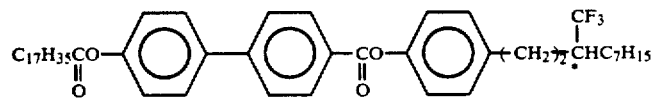 (I-63)
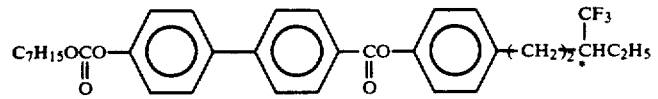 (I-64)
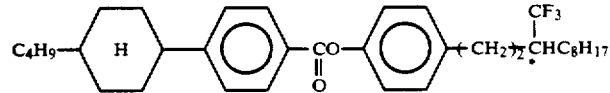 (I-65)
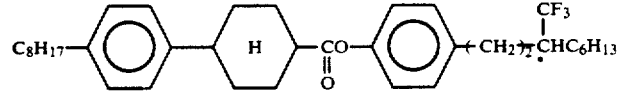 (I-66)
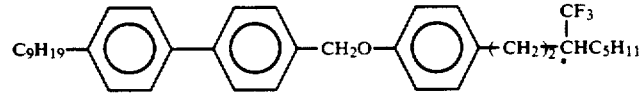 (I-67)
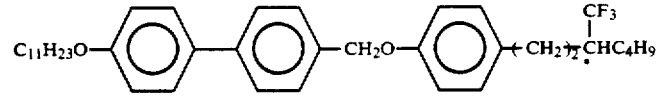 (I-68)
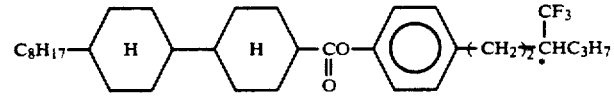 (I-69)
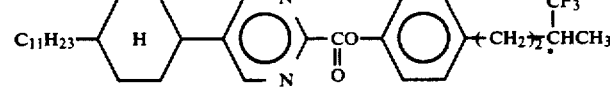 (I-70)
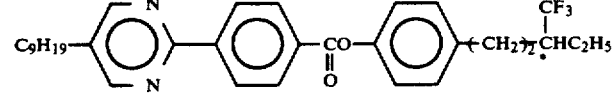 (I-71)
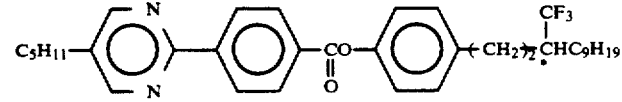 (I-72)
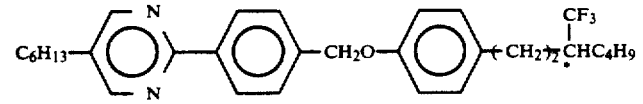 (I-73)

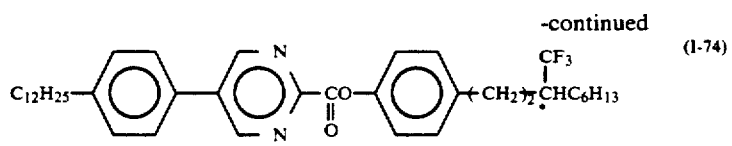
(I-74)
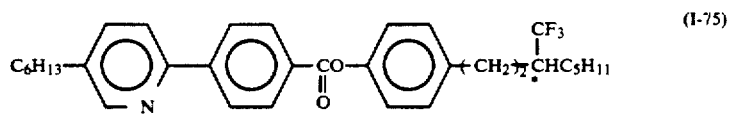
(I-75)
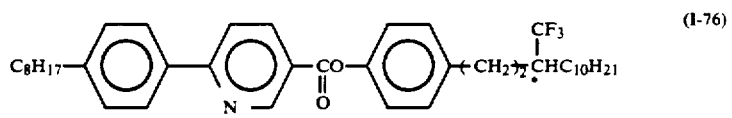
(I-76)
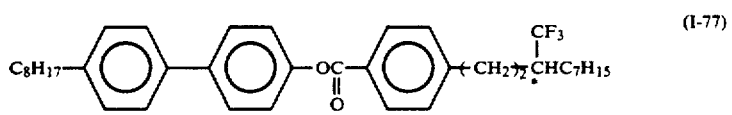
(I-77)
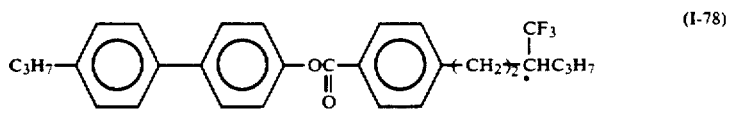
(I-78)
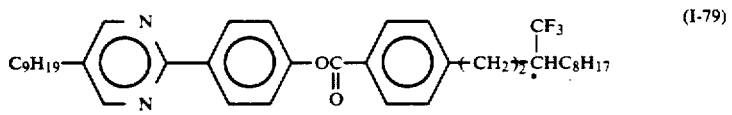
(I-79)
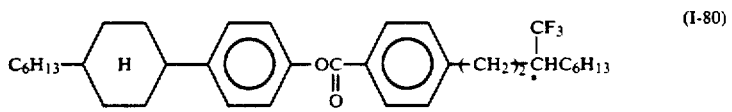
(I-80)
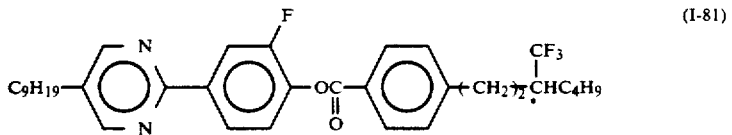
(I-81)
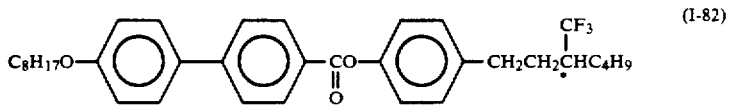
(I-82)
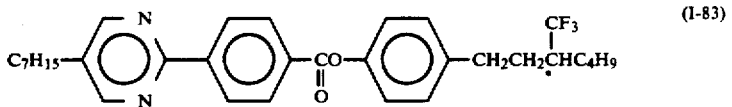
(I-83)
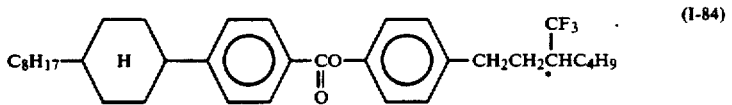
(I-84)
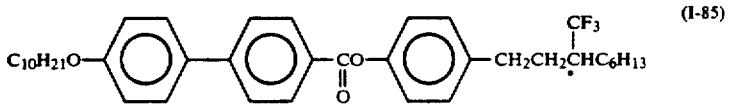
(I-85)
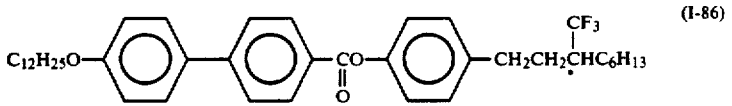
(I-86)

-continued $C_8H_{17}O$-〇-〇-CO-O-〇-$CH_2CH_2\overset{*}{C}H(CF_3)C_6H_{13}$ (I-87)

$C_{12}H_{25}O$-〇-〇-CO-O-〇-$CH_2CH_2\overset{*}{C}H(CF_3)C_4H_9$ (I-88)

$C_{16}H_{33}O$-〇-〇-CO-O-〇-$CH_2CH_2\overset{*}{C}H(CF_3)C_4H_9$ (I-89)

$C_6H_{13}O$-〇-〇-CO-O-〇-$CH_2CH_2\overset{*}{C}H(CF_3)C_4H_9$ (I-90)

$C_7H_{15}$-〇-〇-CO-O-〇-$CH_2CH_2\overset{*}{C}H(CF_3)C_4H_9$ (I-91)

$C_{16}H_{33}O$-〇-〇-CO-O-〇-$CH_2CH_2\overset{*}{C}H(CF_3)C_6H_{13}$ (I-92)

$C_7H_{15}$-〇-〇-CO-O-〇-$CH_2CH_2\overset{*}{C}H(CF_3)C_6H_{13}$ (I-93)

$C_7H_{15}$-(pyrimidine)-〇-CO-O-〇-$CH_2CH_2\overset{*}{C}H(CF_3)C_6H_{13}$ (I-94)

$C_8H_{17}$-(cyclohexane, H)-〇-CO-O-〇-$CH_2CH_2\overset{*}{C}H(CF_3)C_6H_{13}$ (I-95)

$C_6H_{13}O$-〇-〇-CO-O-〇-$CH_2CH_2\overset{*}{C}H(CF_3)C_6H_{13}$ (I-96)

$C_8H_{17}$-〇-(pyrimidine)-〇-$(CH_2)_2\overset{*}{C}H(CF_3)C_6H_{13}$ (I-97)

$C_6H_{13}$-〇-(pyrimidine)-CO-O-〇-$(CH_2)_2\overset{*}{C}H(CF_3)C_4H_9$ (I-98)

$C_7H_{15}O$-(pyrimidine)-〇-$CH_2O$-〇-$(CH_2)_2\overset{*}{C}H(CF_3)C_5H_{11}$ (I-99)

The liquid crystal composition according to the present invention may be obtained by mixing at least one species of the compound represented by the formula (I) and another mesomorphic compound in appropriate proportions. The liquid crystal composition according to the present invention may preferably be formulated as a liquid crystal composition capable of utilizing ferroelectricity, particularly a liquid crystal composition showing a chiral smectic phase.

Another mesomorphic compound as described above may assume a chiral smectic phase or non-chiral smectic phase by itself. When the liquid crystal composition comprising the mesomorphic compound of the formula (I) and another mesomorphic compound mixed therewith assumes a chiral smectic phase, there can be provided the liquid crystal device utilizing ferroelectricity of the liquid crystal composition.

Specific examples of another mesomorphic compound as described above may include those denoted by the following structural formulas.

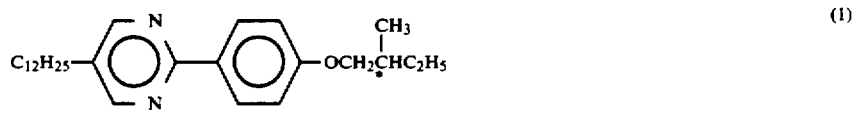

(1)

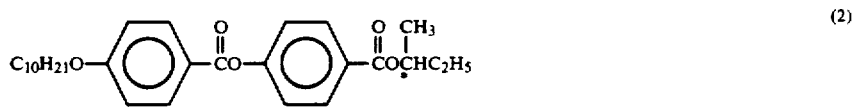

(2)

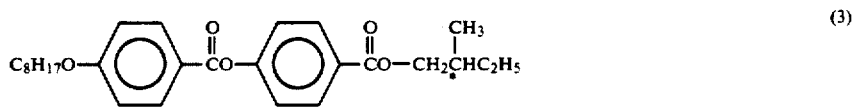

(3)

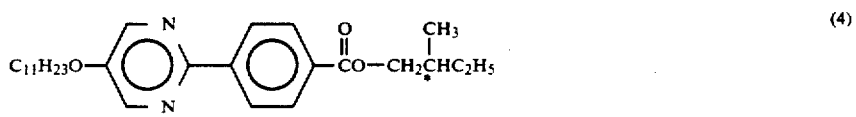

(4)

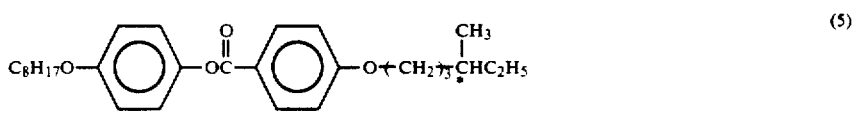

(5)

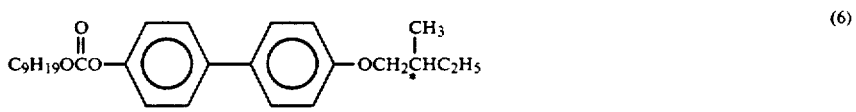

(6)

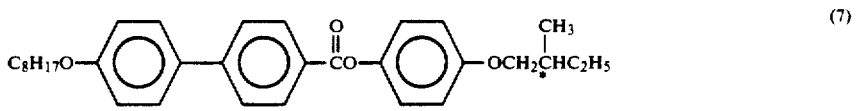

(7)

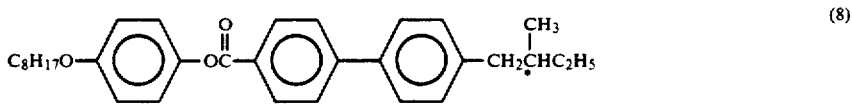

(8)

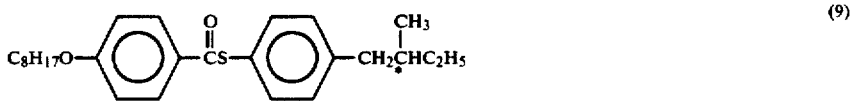

(9)

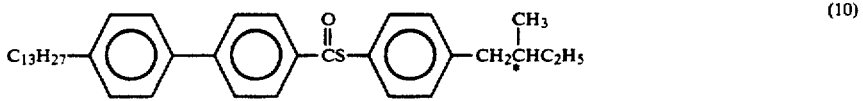

(10)

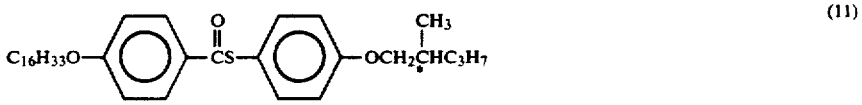

(11)

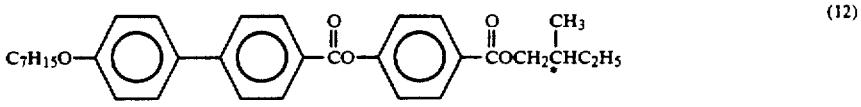

(12)

-continued
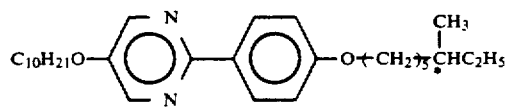 (13)
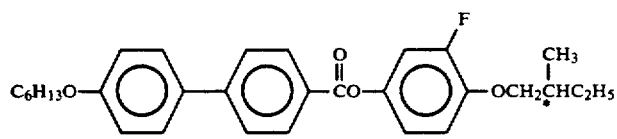 (14)
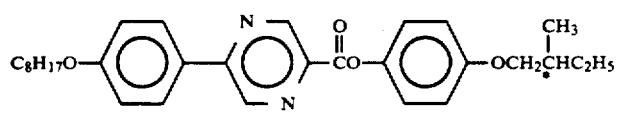 (15)
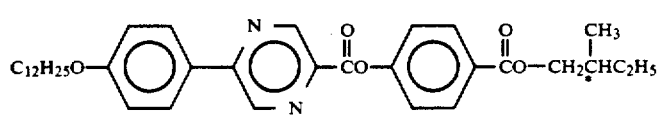 (16)
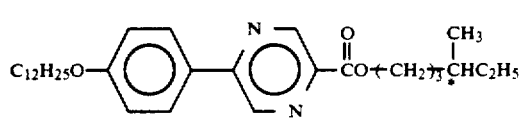 (17)
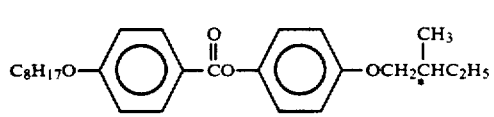 (18)
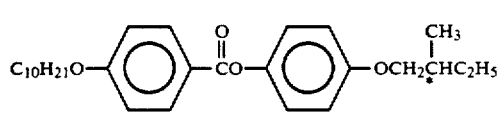 (19)
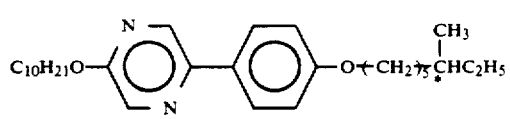 (20)
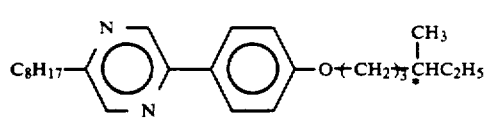 (21)
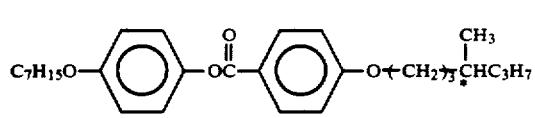 (22)
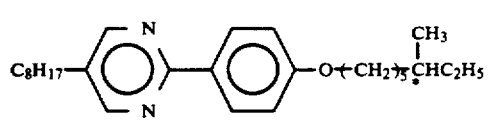 (23)
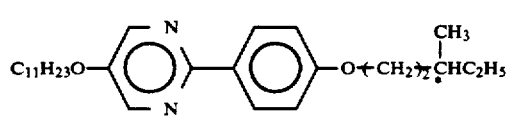 (24)
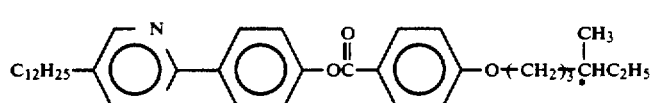 (25)

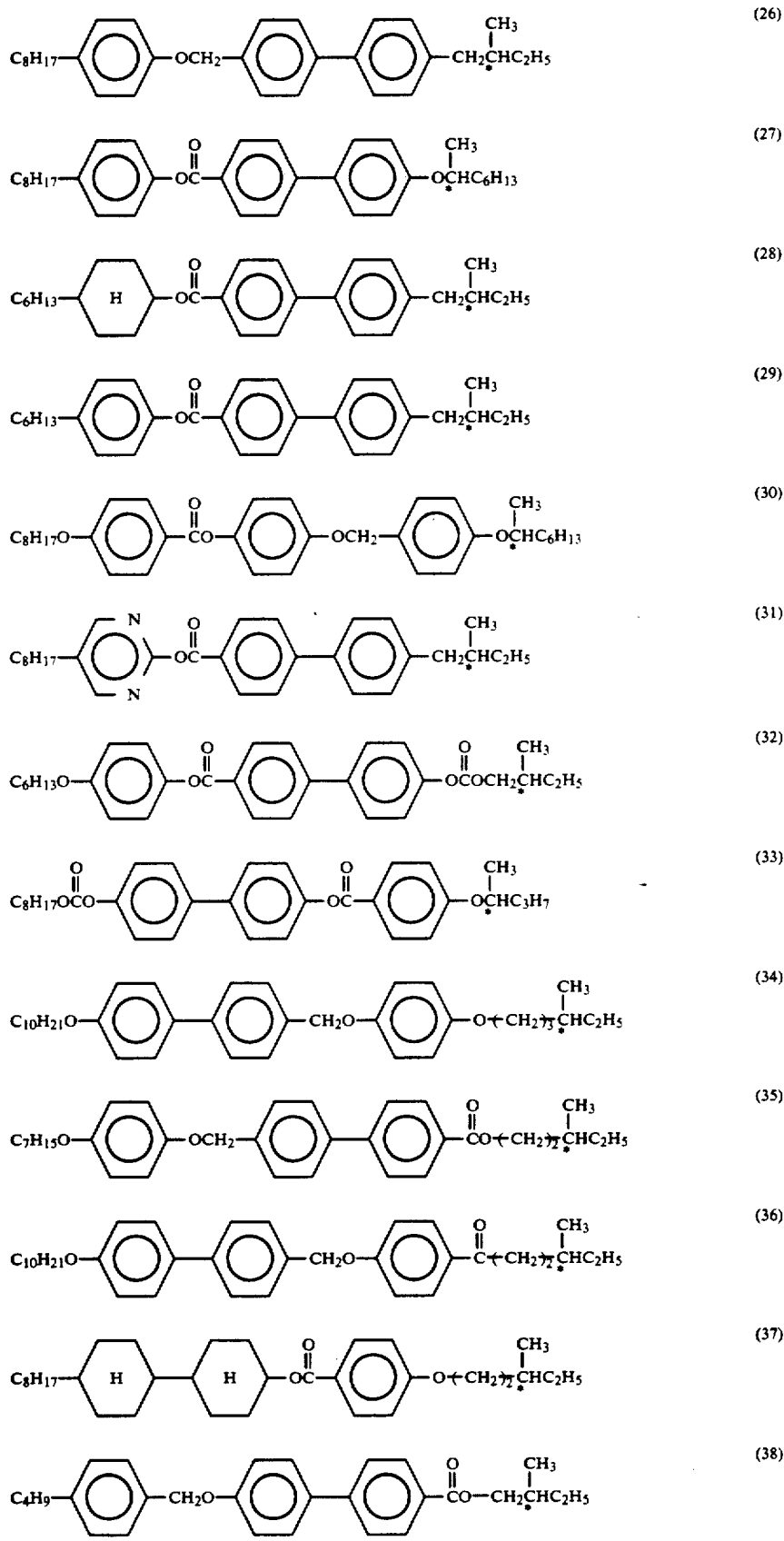

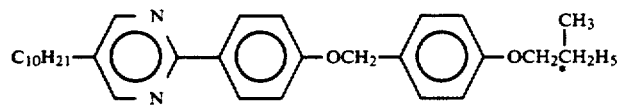
(39)
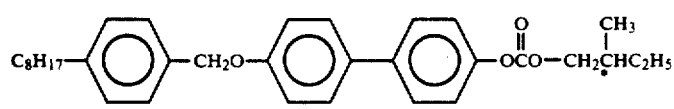
(40)
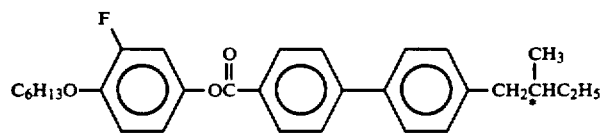
(41)
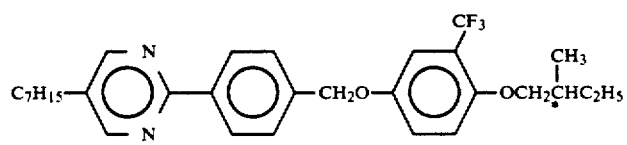
(42)
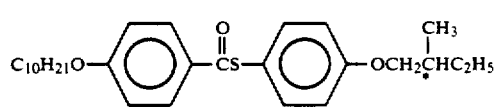
(43)
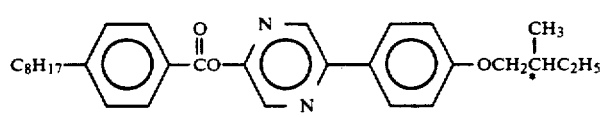
(44)
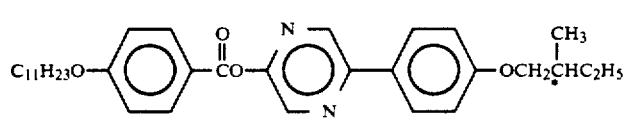
(45)
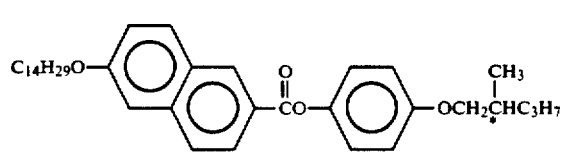
(46)
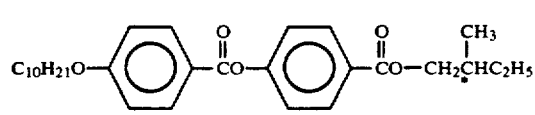
(47)
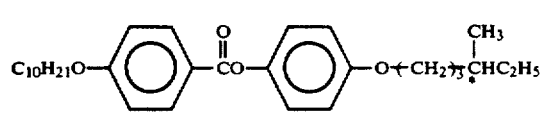
(48)
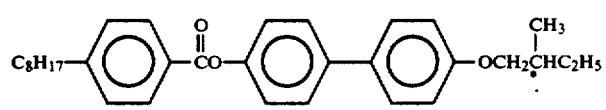
(49)
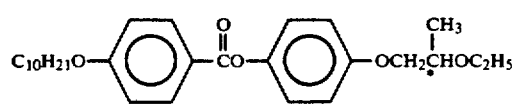
(50)
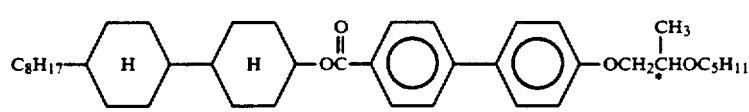
(51)

-continued
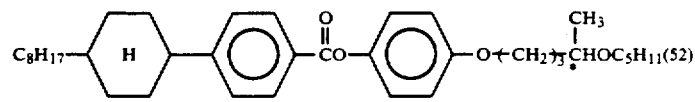
(52)
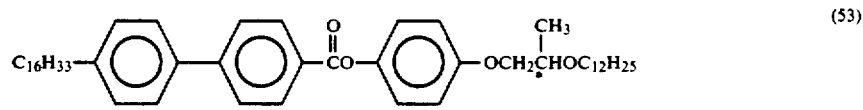
(53)
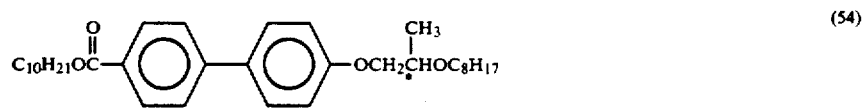
(54)
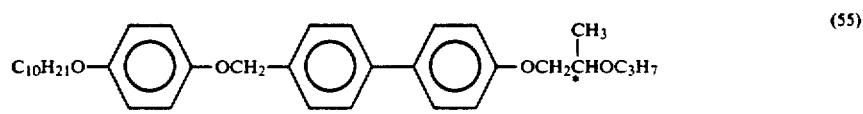
(55)
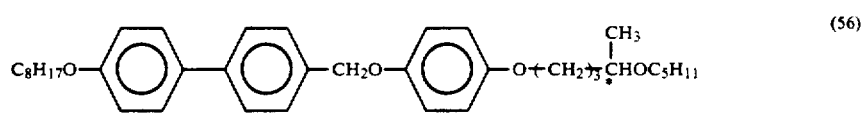
(56)
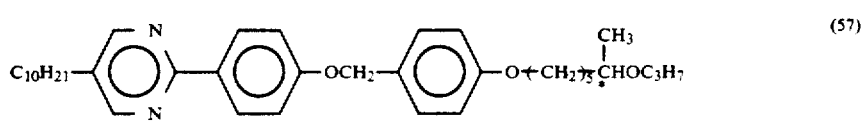
(57)
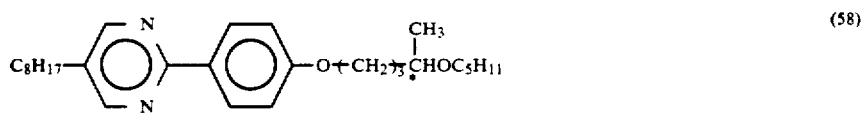
(58)
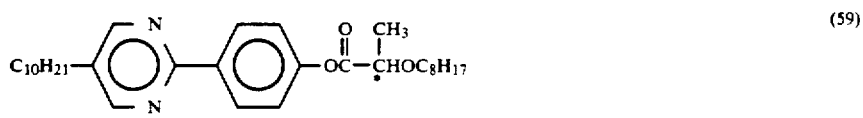
(59)
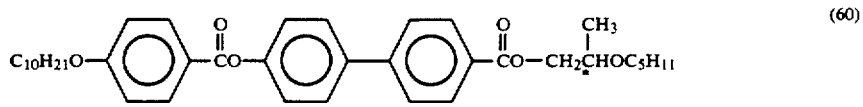
(60)
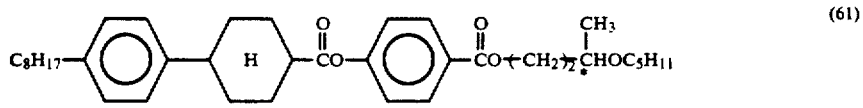
(61)
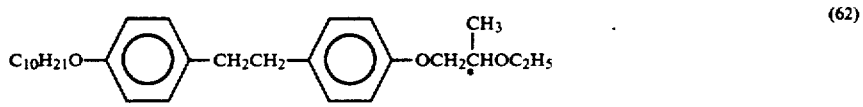
(62)
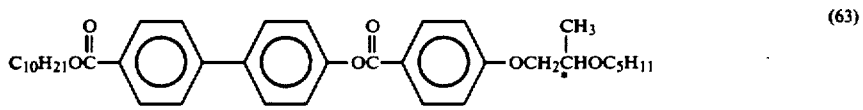
(63)
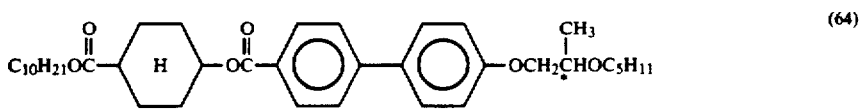
(64)

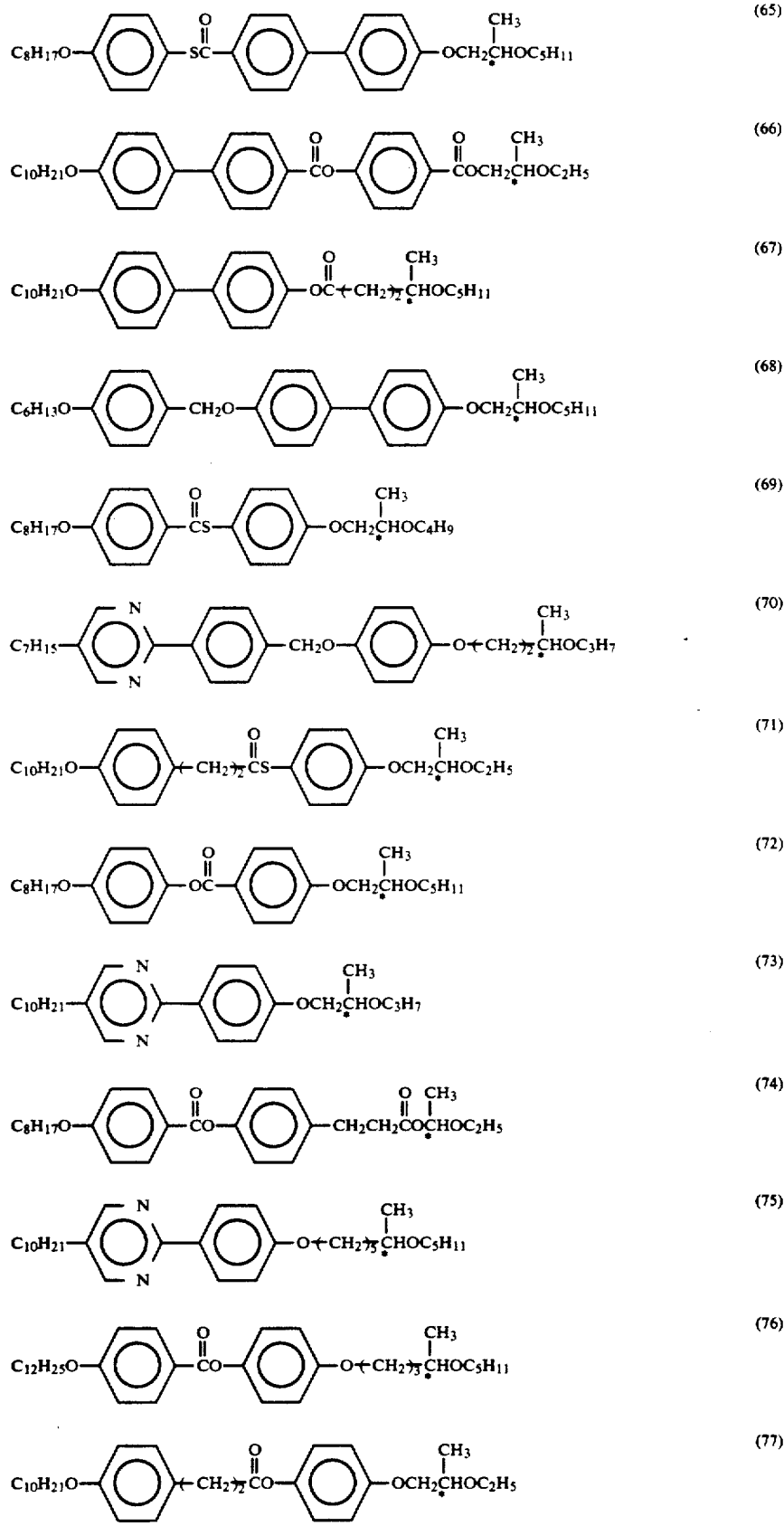

-continued
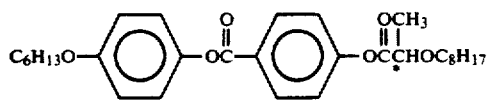
(78)
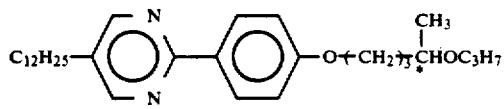
(79)
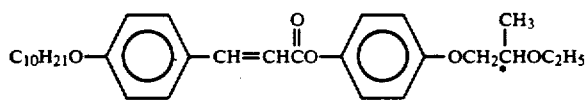
(80)
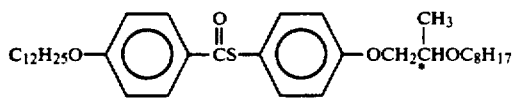
(81)
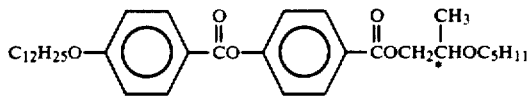
(82)
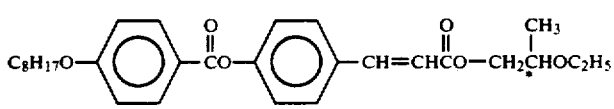
(83)
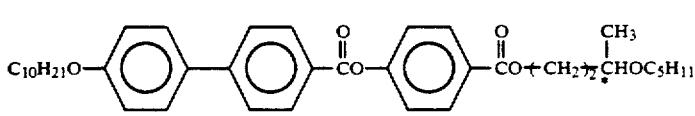
(84)
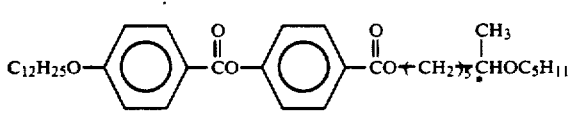
(85)
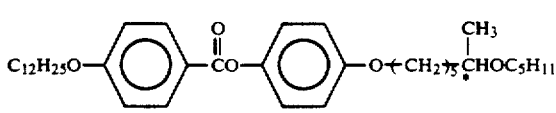
(86)
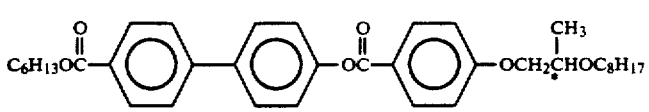
(87)
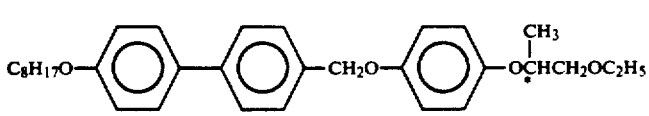
(88)
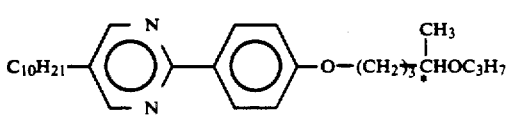
(89)
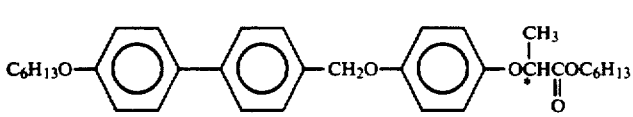
(90)

-continued
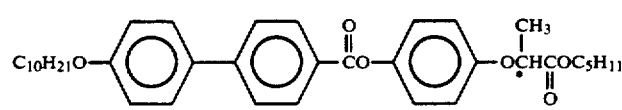 (91)
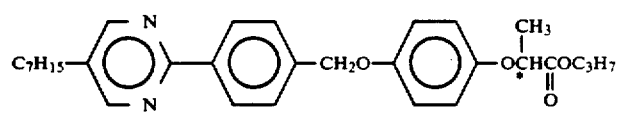 (92)
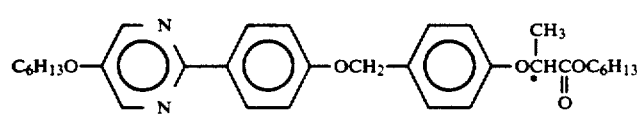 (93)
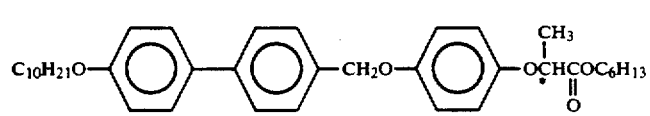 (94)
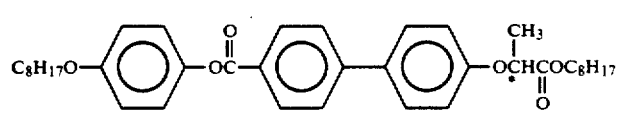 (95)
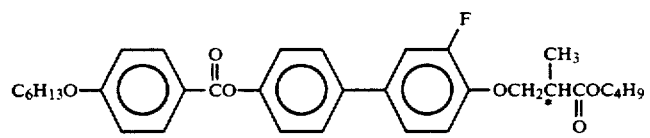 (96)
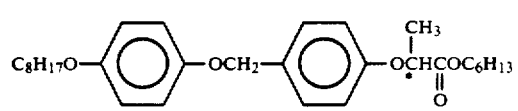 (97)
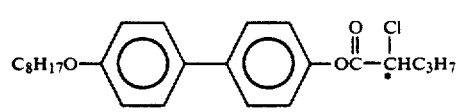 (98)
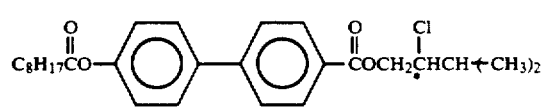 (99)
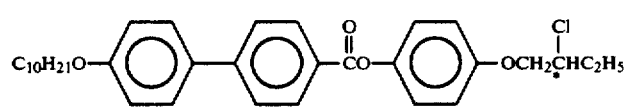 (100)
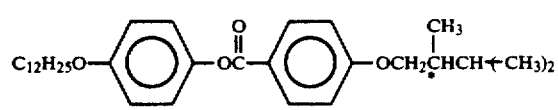 (101)
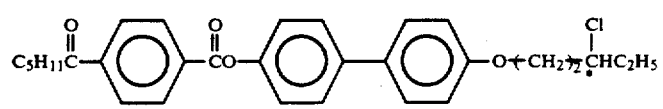 (102)
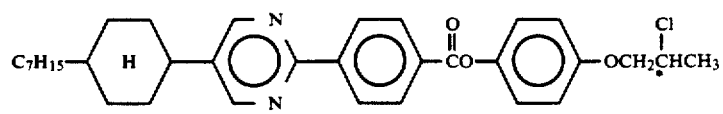 (103)

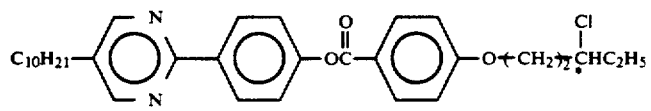 (104)
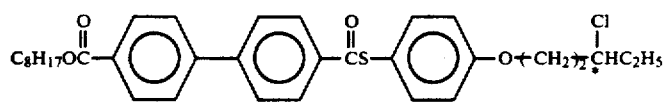 (105)
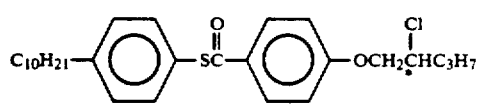 (106)
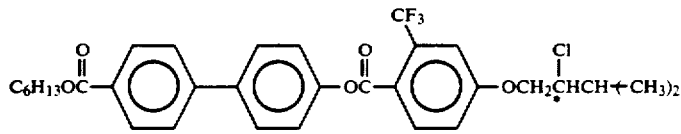 (107)
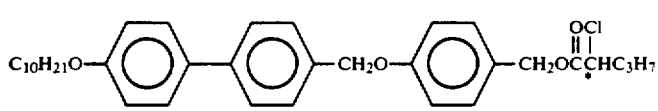 (108)
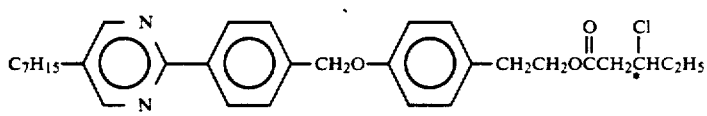 (109)
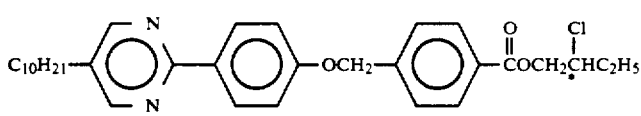 (110)
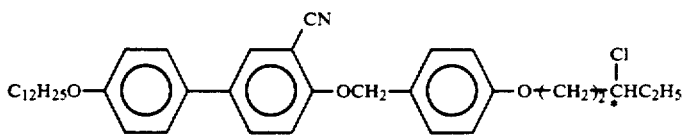 (111)
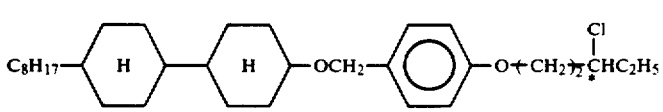 (112)
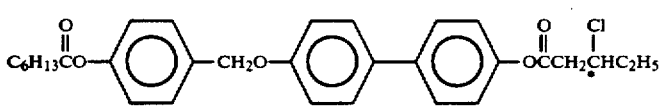 (113)
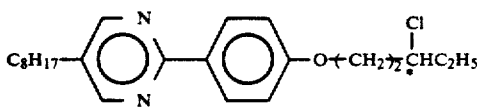 (114)
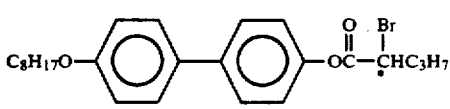 (115)
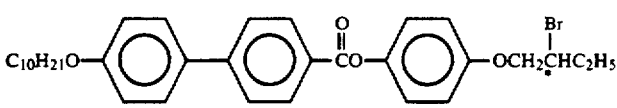 (116)

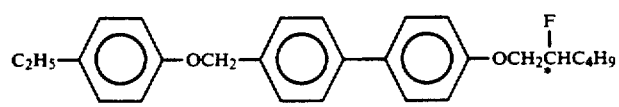 (117)
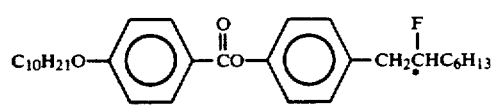 (118)
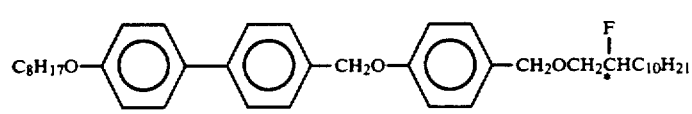 (119)
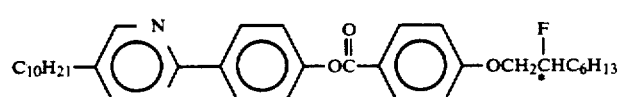 (120)
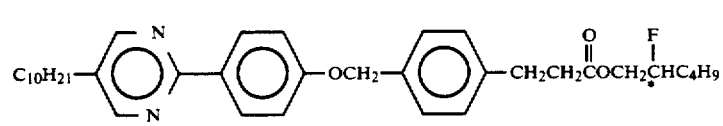 (121)
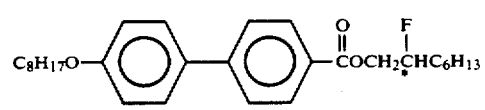 (122)
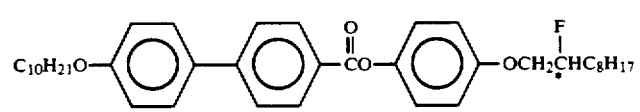 (123)
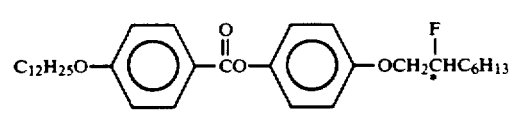 (124)
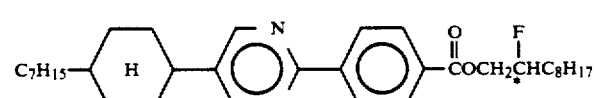 (125)
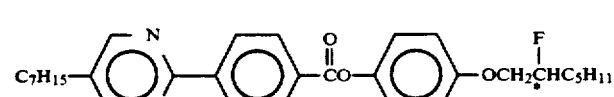 (126)
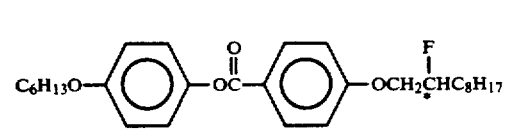 (127)
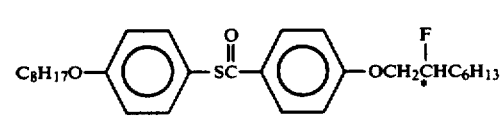 (128)
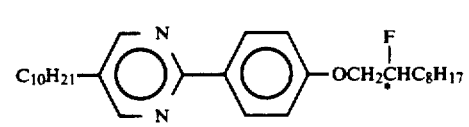 (129)

-continued
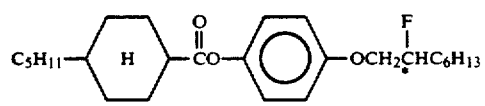
(130)
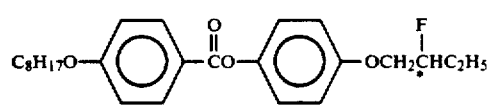
(131)
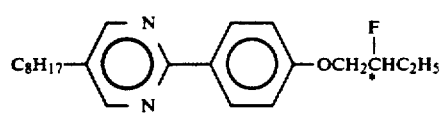
(132)
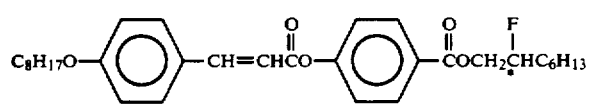
(133)
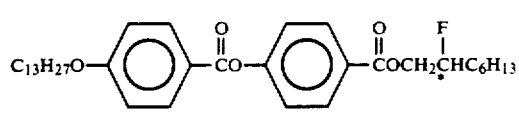
(134)
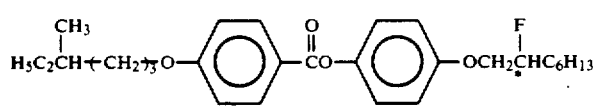
(135)
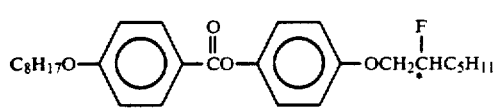
(136)
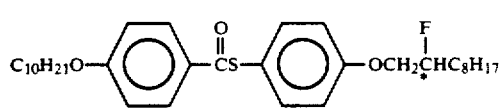
(137)
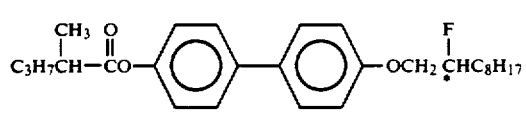
(138)
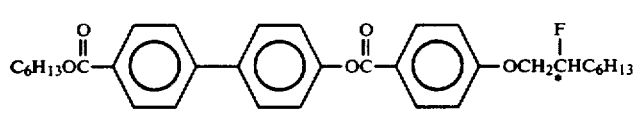
(139)
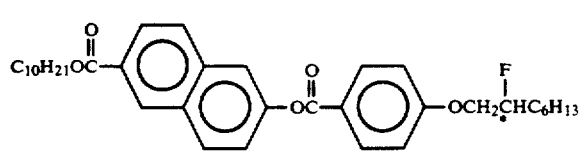
(140)
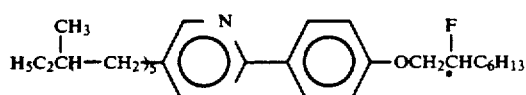
(141)
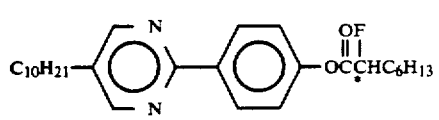
(142)

-continued
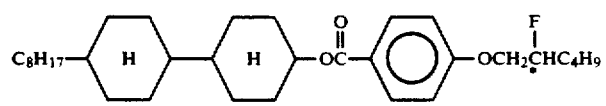
(143)
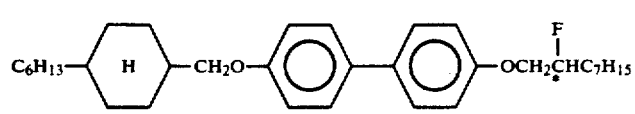
(144)
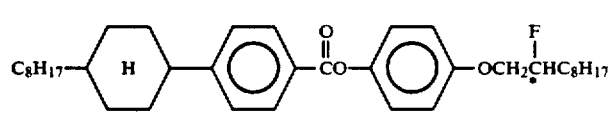
(145)
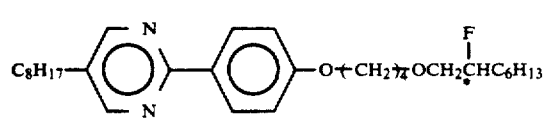
(146)
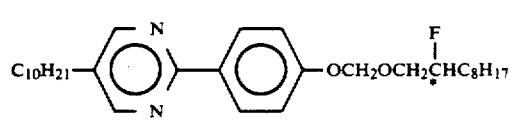
(147)
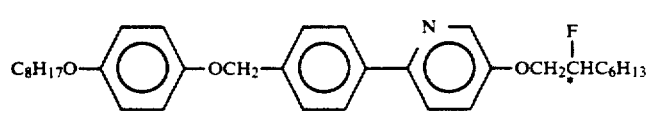
(148)
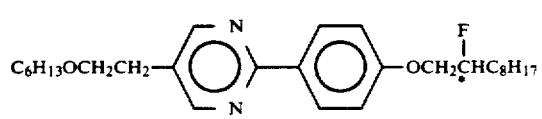
(149)
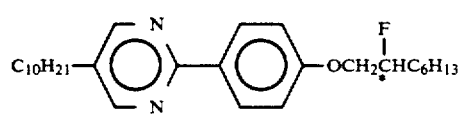
(150)
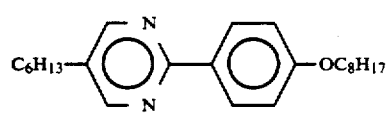
(151)
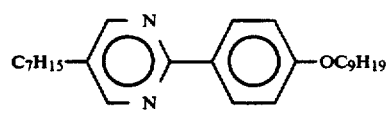
(152)
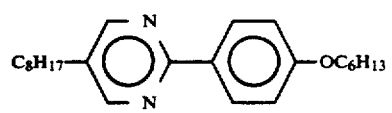
(153)
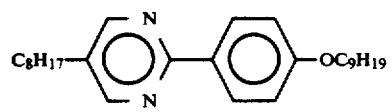
(154)
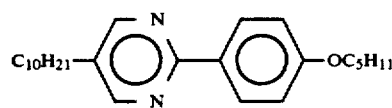
(155)

-continued
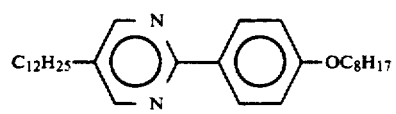 (156)
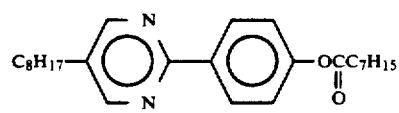 (157)
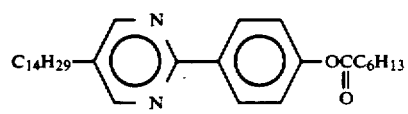 (158)
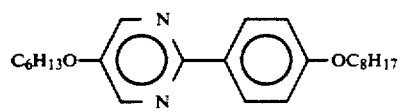 (159)
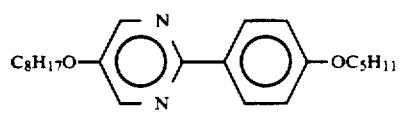 (160)
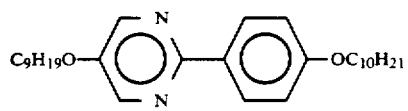 (161)
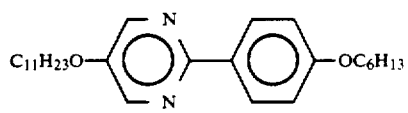 (162)
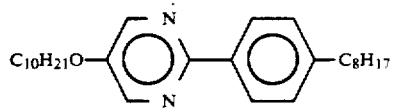 (163)
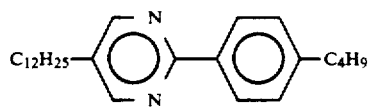 (164)
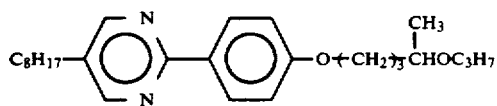 (165)
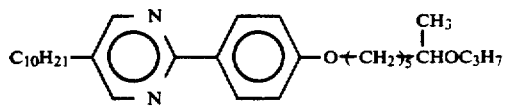 (166)
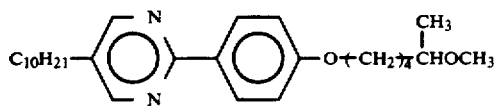 (167)
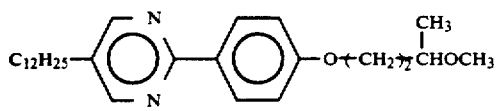 (168)

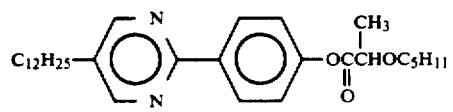 (169)
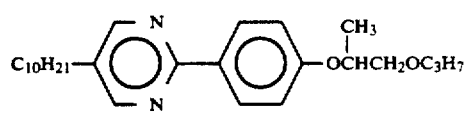 (170)
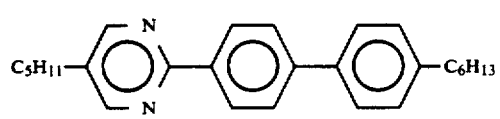 (171)
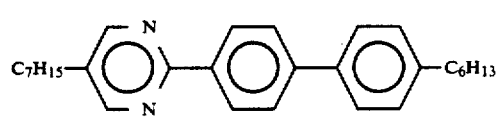 (172)
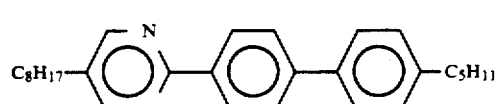 (173)
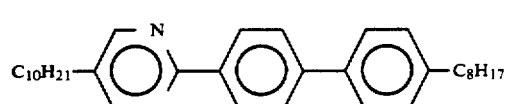 (174)
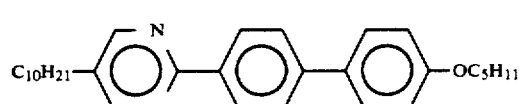 (175)
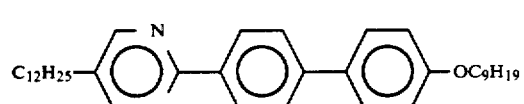 (176)
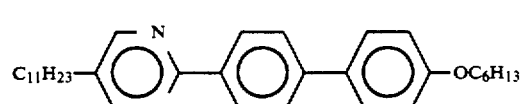 (177)
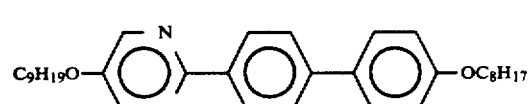 (178)
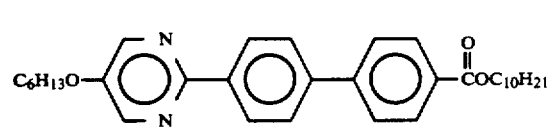 (179)
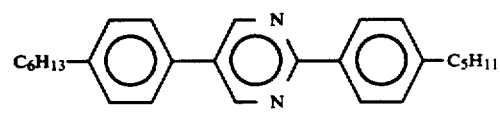 (180)
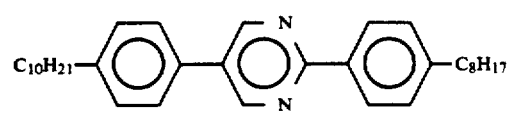 (181)

-continued
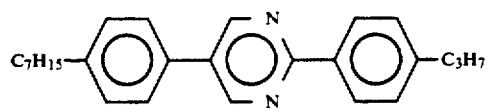 (182)
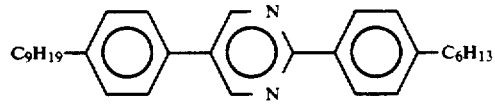 (183)
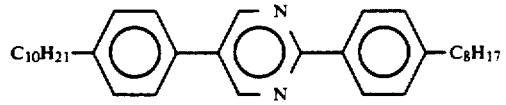 (184)
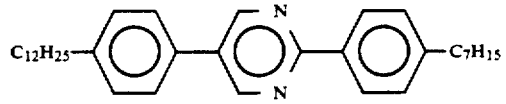 (185)
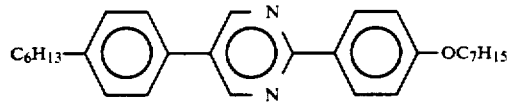 (186)
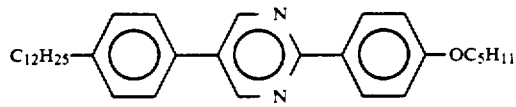 (187)
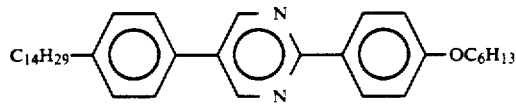 (188)
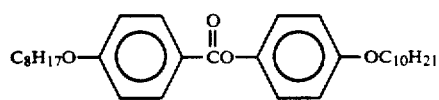 (189)
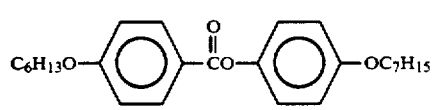 (190)
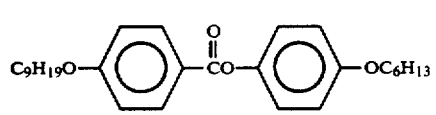 (191)
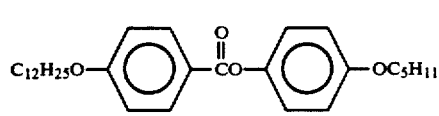 (192)
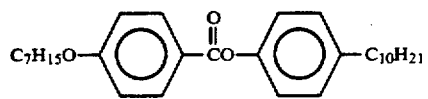 (193)
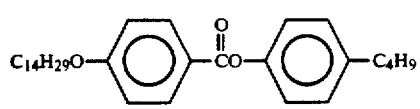 (194)

-continued
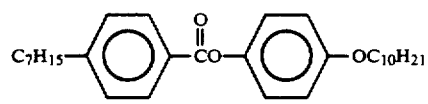 (195)
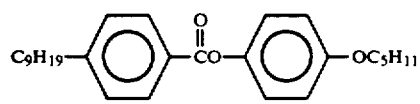 (196)
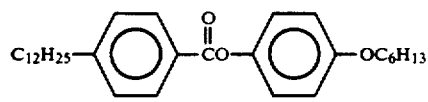 (197)
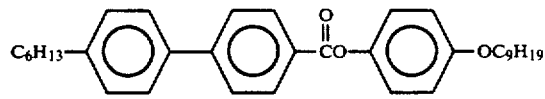 (198)
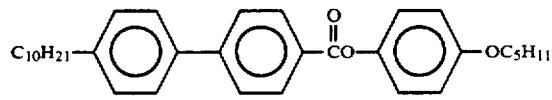 (199)
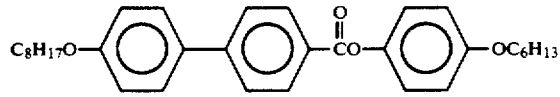 (200)
 (201)
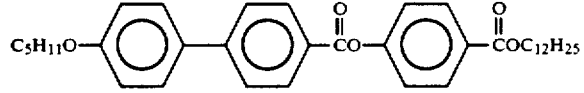 (202)
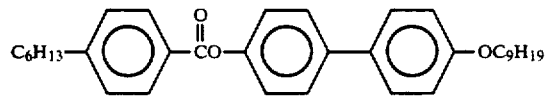 (203)
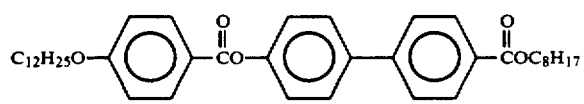 (204)
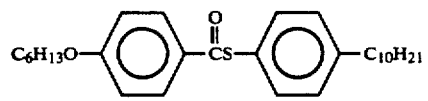 (205)
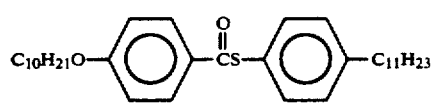 (206)
 (207)
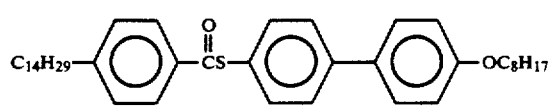 (208)

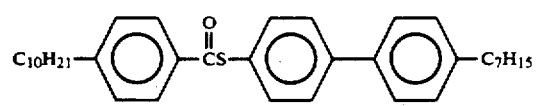 (209)
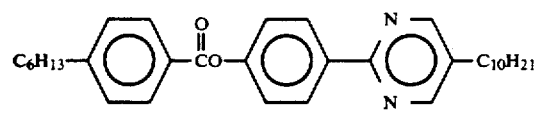 (210)
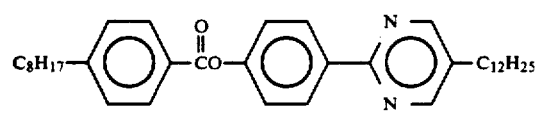 (211)
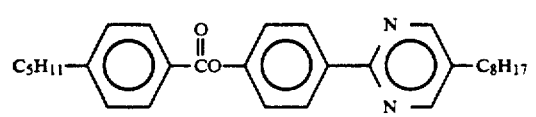 (212)
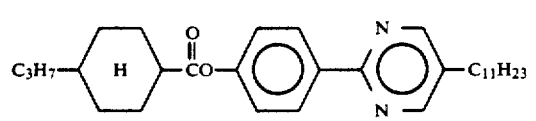 (213)
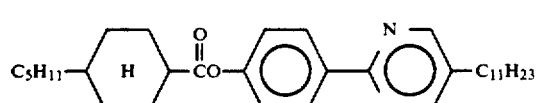 (214)
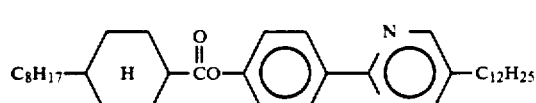 (215)
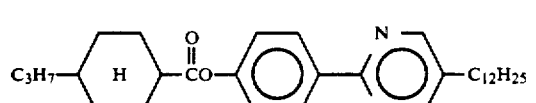 (216)
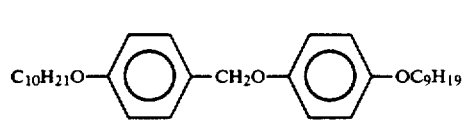 (217)
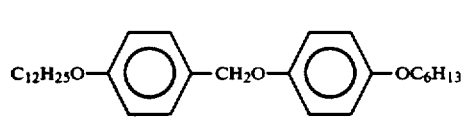 (218)
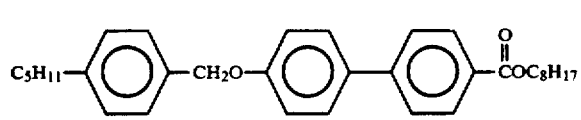 (219)
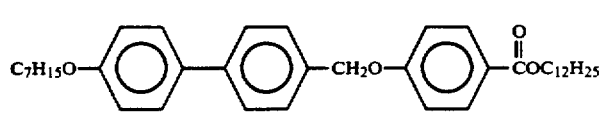 (220)
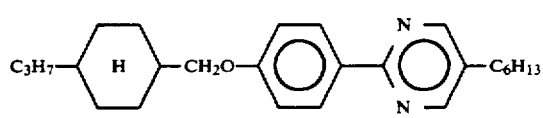 (221)

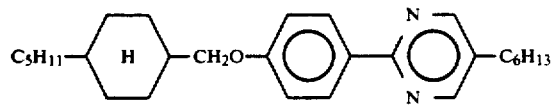
(222)
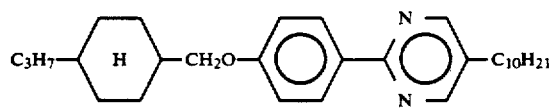
(223)
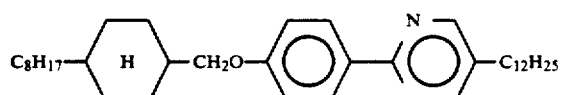
(224)
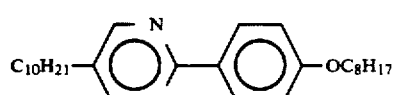
(225)
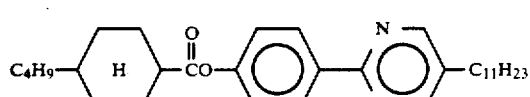
(226)
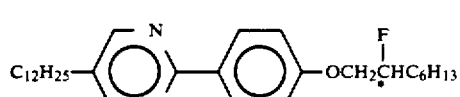
(227)
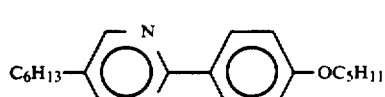
(228)
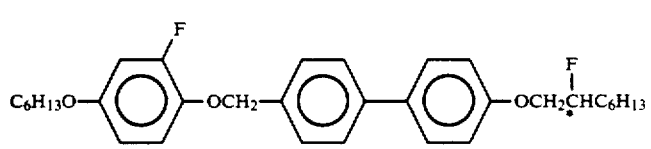
(229)
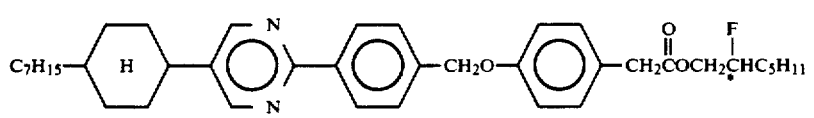
(230)
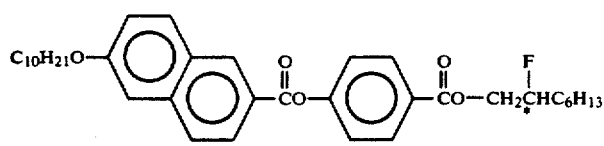
(231)
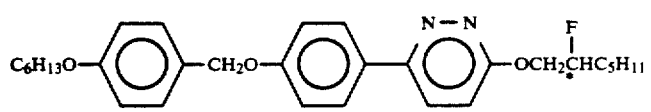
(232)
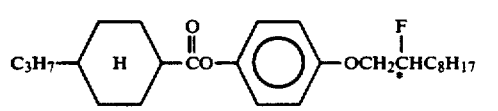
(233)
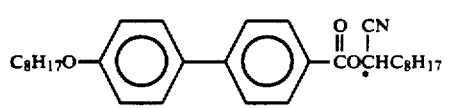
(234)

-continued

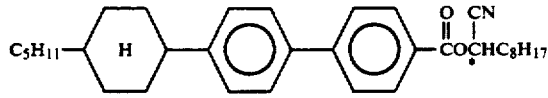
(235)

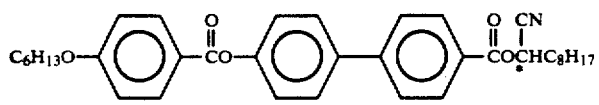
(236)

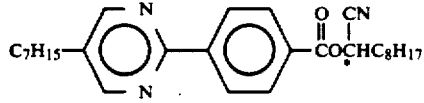
(237)

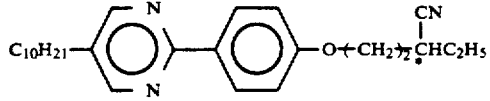
(238)

In formulating the liquid crystal composition according to the present invention, it is desirable to mix 1-500 wt. parts, preferably 2-200 wt. parts, more preferably 3-80 wt. parts, of a compound represented by the formula (I) with 100 wt. parts of at least one species of another mesomorphic compound other than the compound represented by the formula (I).

Alternatively, the liquid crystal composition may desirably contain 1-80 wt. %, preferably 1-60 wt. %, more preferably 1-40 wt. % of a mesomorphic compound represented by the formula (I).

Further, when two or more species of the compounds represented by the formula (I) are used, the two or more species of the compounds of the formula (I) may be used in a total amount of 1-500 wt. parts, preferably 2-200 wt. parts, more preferably 3-80 wt. parts, per 100 wt. parts of at least one species of another mesomorphic compound other than the two or more species of the compounds of the formula (I).

Alternatively, the liquid crystal composition may desirably contain 1-80 wt. %, preferably 1-60 wt. %, more preferably 1-40 wt. %, of the two or more species of the compounds represented by the formula (I).

The liquid crystal device according to the present invention may preferably be prepared by heating the liquid crystal composition prepared as described above into an isotropic liquid under vacuum, filling a blank cell comprising a pair of oppositely spaced electrode plates with the composition, gradually cooling the cell to form a liquid crystal layer and restoring the normal pressure.

FIG. 1 is a schematic sectional view of an embodiment of the liquid crystal device utilizing ferroelectricity prepared as described above for explanation of the structure thereof.

Referring to FIG. 1, the liquid crystal device includes a liquid crystal layer 1 assuming a chiral smectic phase disposed between a pair of glass substrates 2 each having thereon a transparent electrode 3 and a insulating alignment control layer 4. Lead wires 6 are connected to the electrodes so as to apply a driving voltage to the liquid crystal layer 1 from a power supply 7. Outside the substrates 2, a pair of polarizers 8 are disposed so as to modulate incident light I₀ from a light source 9 in cooperation with the liquid crystal 1 to provide modulated light I.

Each of two glass substrates 2 is coated with a transparent electrode 3 comprising a film of In₂O₃, SnO₂ or ITO (indium-tin-oxide) to form an electrode plate. Further thereon, an insulating alignment control layer 4 is formed by rubbing a film of a polymer such as polyimide with gauze or acetate fiber-planted cloth so as to align the liquid crystal molecules in the rubbing direction. Further, it is also possible to compose the alignment control layer of two layers, e.g., by first forming an insulating layer of an inorganic material, such as silicon nitride, silicon nitride containing hydrogen, silicon carbide, silicon carbide containing hydrogen, silicon oxide, boron nitride, boron nitride containing hydrogen, cerium oxide, aluminum oxide, zirconium oxide, titanium oxide, or magnesium fluoride, and forming thereon an alignment control layer of an organic insulating material, such as polyvinyl alcohol, polyimide, polyamide-imide, polyester-imide, polyparaxylylene, polyester, polycarbonate, polyvinyl acetal, polyvinyl chloride, polyvinyl acetate, polyamide, polystyrene, cellulose resin, melamine resin, urea resin, acrylic resin, or photoresist resin. Alternatively, it is also possible to use a single layer of inorganic insulating alignment control layer or organic insulating alignment control layer. An inorganic insulating alignment control layer may be formed by vapor deposition, while an organic insulating alignment control layer may be formed by applying a solution of an organic insulating material or a precursor thereof in a concentration of 0.1 to 20 wt. %, preferably 0.2-10 wt. %, by spinner coating, dip coating, screen printing, spray coating or roller coating, followed by curing or hardening under prescribed hardening condition (e.g., by heating). The insulating alignment control layer may have a thickness of ordinarily 30 Å-1 micron, preferably 30-3000 Å, further preferably 50-1000 Å. The two glass substrates 2 with transparent electrodes 3 (which may be inclusively referred to herein as "electrode plates") and further with insulating alignment control layers 4 thereof are held to have a prescribed (but arbitrary) gap with a spacer 5. For example, such a cell structure with a prescribed gap may be formed by sandwiching spacers of silica beads or alumina beads having a prescribed diameter with two glass plates, and then sealing the periphery thereof with, e.g., an epoxy adhesive. Alternatively, a polymer film or glass fiber may also be used as a spacer. Between the two glass plates, a liquid crystal assuming a chiral smectic phase is sealed up to provide a liquid crystal layer 1 in a thickness of generally 0.5 to 20 microns, preferably 1 to 5 microns.

The liquid crystal provided by the composition of the present invention may desirably assume a SmC* phase (chiral smectic C phase) in a wide temperature range including room temperature (particularly, broad in a lower temperature side) and also shows wide drive voltage margin and drive temperature margin when contained in a device.

Particularly, in order to show a good alignment characteristic to form a uniform monodomain, the ferroelectric liquid crystal may show a phase transition series comprising isotropic phase-Ch phase (cholesteric phase)-SmA phase (smectic A phase)-SmC* phase (chiral smectic C phase) on temperature decrease.

The transparent electrodes 3 are connected to the external power supply 7 through the lead wires 6. Further, outside the glass substrates 2, polarizers 8 are applied. The device shown in FIG. 1 is of a transmission type and is provided with a light source 9.

Figure 3:
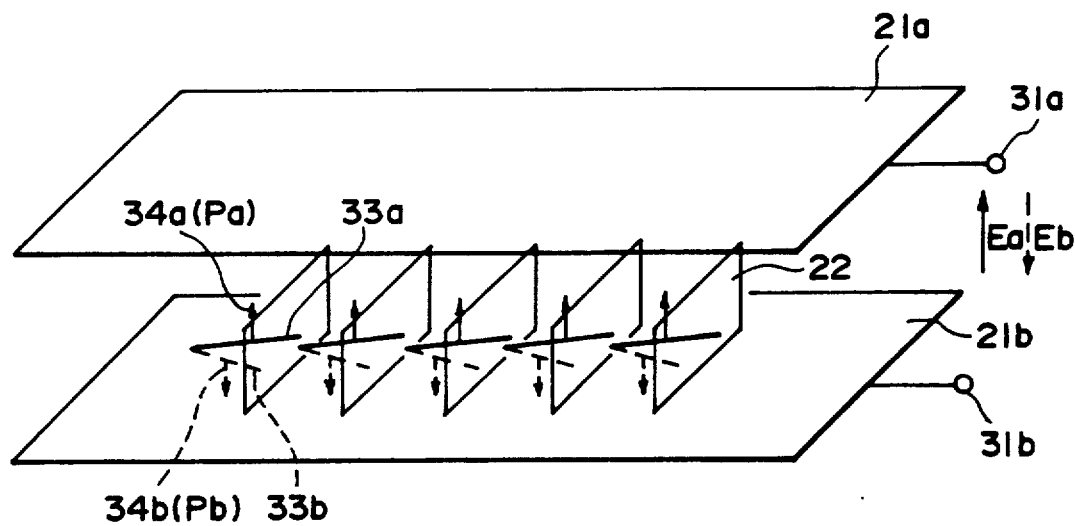

FIG. 2 is a schematic illustration of a liquid crystal cell (device) utilizing ferroelectricity for explaining operation thereof. Reference numerals 21a and 21b denote substrates (glass plates) on which a transparent electrode of, e.g., $In_2O_3$, $SnO_2$, ITO (indium-tin-oxide), etc., is disposed, respectively. A liquid crystal of an SmC*-phase (chiral smectic C phase) or SmH*-phase (chiral smectic H phase) in which liquid crystal molecular layers 22 are aligned perpendicular to surfaces of the glass plates is hermetically disposed therebetween. Full lines 23 show liquid crystal molecules. Each liquid crystal molecule 23 has a dipole moment ($P_1$) 24 in a direction perpendicular to the axis thereof. The liquid crystal molecules 23 continuously form a helical structure in the direction of extension of the substrates. When a voltage higher than a certain threshold level is applied between electrodes formed on the substrates 21a and 21b, a helical structure of the liquid crystal molecule 23 is unwound or released to change the alignment direction of respective liquid crystal molecules 23 so that the dipole moments ($P_1$) 24 are all directed in the direction of the electric field. The liquid crystal molecules 23 have an elongated shape and show refractive anisotropy between the long axis and the short axis thereof Accordingly, it is easily understood that when, for instance, polarizers arranged in a cross nicol relationship, i e., with their polarizing directions crossing each other, are disposed on the upper and the lower surfaces of the glass plates, the liquid crystal cell thus arranged functions as a liquid crystal optical modulation device of which optical characteristics vary depending upon the polarity of an applied voltage Further, when the liquid crystal cell is made sufficiently thin (e.g., less than about 10 microns), the helical structure of the liquid crystal molecules is unwound to provide a non-helical structure eve in the absence of an electric field, whereby the dipole moment assumes either of the two states, i.e., Pa in an upper direction 34a or Pb in a lower direction 34b as shown in FIG. 3, thus providing a bistable condition. When an electric field Ea or Eb higher than a certain threshold level and different from each other in polarity as shown in FIG. 3 is applied to a cell having the above-mentioned characteristics by using voltage application means 31a and 31b, the dipole moment is directed either in the upper direction 34a or in the lower direction 34b depending on the vector of the electric field Ea or Eb. In correspondence with this, the liquid crystal molecules are oriented in either of a first stable state 33a and a second stable state 33b.

When the above-mentioned ferroelectric liquid crystal is used as an optical modulation element, it is possible to obtain two advantages. First is that the response speed is quite fast. Second is that the orientation of the liquid crystal shows bistability. The second advantage will be further explained, e.g., with reference to FIG. 3. When the electric field Ea is applied to the liquid crystal molecules, they are oriented in the first stable state 33a. This state is stably retained even if the electric field is removed. On the other hand, when the electric field Eb of which direction is opposite to that of the electric field Ea is applied thereto, the liquid crystal molecules are oriented to the second stable state 33b, whereby the directions of molecules are changed. This state is similarly stably retained even if the electric field is removed. Further, as long as the magnitude of the electric field Ea or Eb being applied is not above a certain threshold value, the liquid crystal molecules are placed in the respective orientation states.

Figure 4:
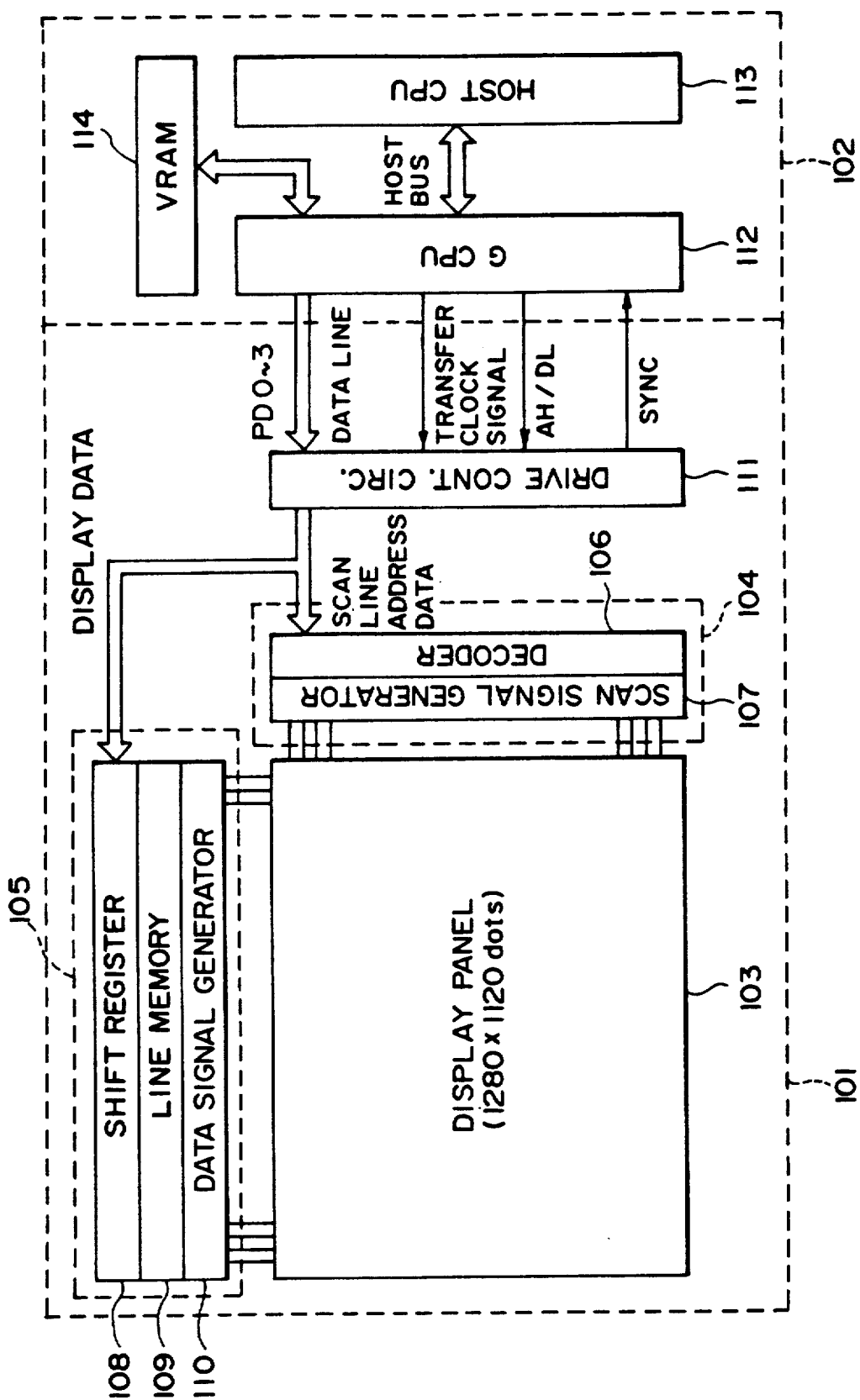
FIG. 4 is a block diagram showing a display apparatus comprising a liquid crystal device utilizing ferroelectricity of a liquid crystal composition and a graphic controller.
Figure 5:
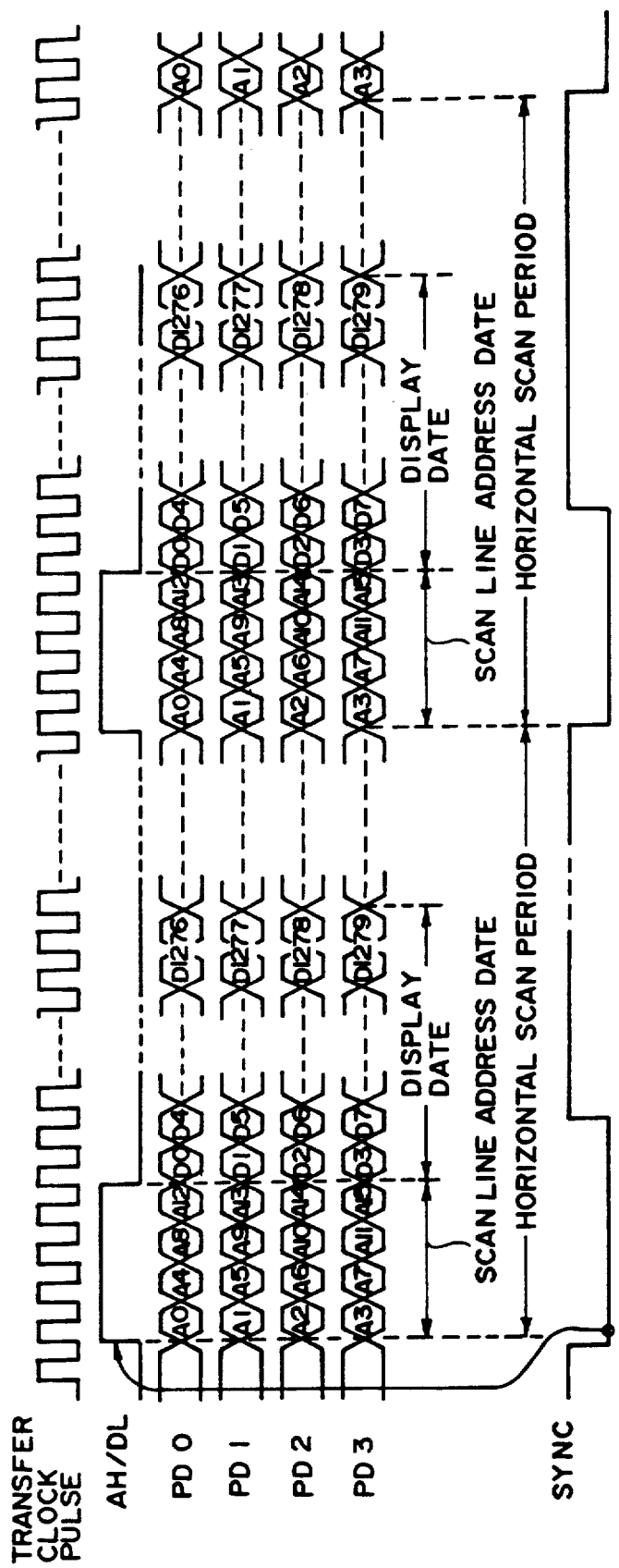
FIG. 5 is a time chart of image data communication showing time correlation between signal transfer and driving with respect to a liquid crystal display apparatus and a graphic controller.

Based on the arrangement and data format comprising image data accompanied with scanning line address data and by adopting communication synchronization using a SYNC signal as shown in FIGS. 4 and 5, there is provided a liquid crystal display apparatus of the present invention which uses the liquid crystal device according to the present invention as a display panel portion.

Image data are generated in a graphic controller 102 in an apparatus body and transferred to a display panel 103 by signal transfer means shown in FIGS. 4 and 5. The graphic controller 102 principally comprises a CPU (central processing unit, hereinafter referred to as "GCPU") 112 and a VRAM (video-RAM, image data storage memory) 114 and is in charge of management and communication of image data between a host CPU 113 and the liquid crystal display apparatus (FLCD) 101. The control method according to the present invention is principally realized in the graphic controller 102.

A light source is disposed at the back of the display panel 103.

Hereinbelow, the present invention will be explained more specifically with reference to examples. It is however to be understood that the present invention is not restricted to these examples.

EXAMPLE 1

4-decyloxybiphenyl-4'-carboxylic acid-4"-(3-trifluoromethylheptyl)phenyl ester (Example Compound No. I-62) was synthesized through the following steps i)-iv).

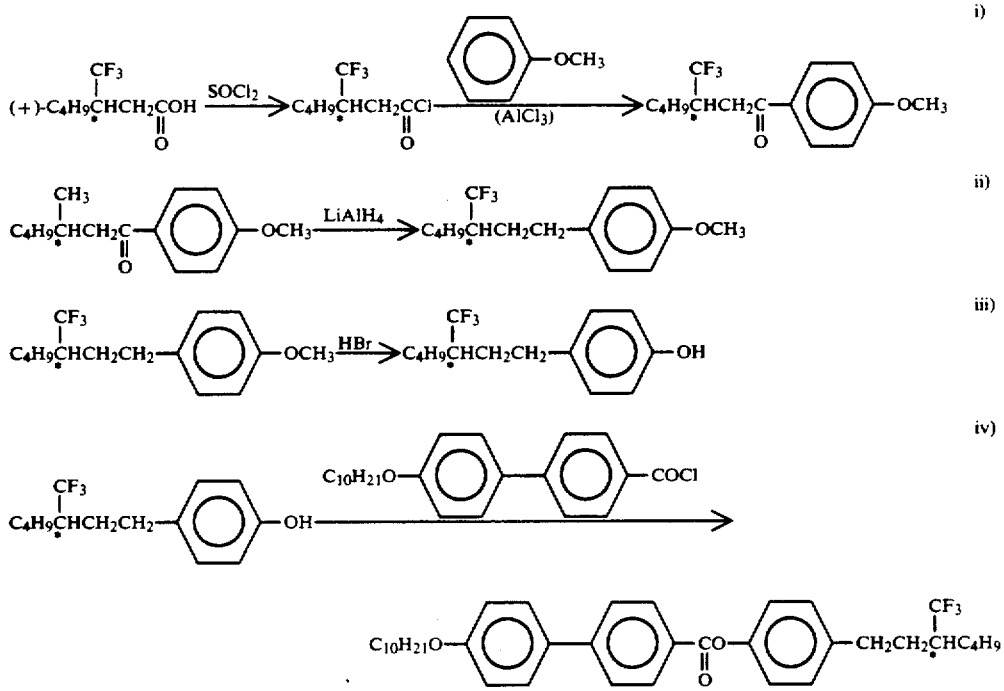

Step i) Production of 4-(3-trifluoromethylheptanoyl)anisole

To a mixture of 4 5 ml of carbon disulfide, 0.33 g of anisole and 0.6 g of aluminum chloride, and acid chloride obtained by reaction of 0.6 g of (+)-3-trifluoromethylheptanoic acid and 4 ml of thionyl chloride was added, followed by heating to 50° C. and stirring for 1 hour. After the reaction, the reaction mixture was cooled on an ice bath and acidified with hydrochloric acid, followed by extraction with diethyl ether. The ether layer was washed with sodium hydrogencarbonate aqueous solution and dried with anhydrous sodium sulfate, followed by distilling-off of the solvent and further distilling under reduced pressure to obtain 0.48 g of 4-(3-trifluoromethylheptanoyl)anisole (Yield: 55 %, b.p. = 140°-150° C./0.45 mmHg).

Step ii) Production of 4-(3-trifluoromethylheptyl)anisole

To a mixture of 0.1 g of aluminum lithium hydride and 2.5 ml of dry diethyl ether, 0.275 g of aluminum chloride and 2.5 ml of dry diethyl ether were added under stirring. To the resultant mixture, a solution of 0.48 g of the above-prepared 4-(3-trifluoromethylheptanoyl)anisole in 2.5 ml of diethyl ether, followed by heat-refluxing for 30 minutes. After the reaction, 5 ml of 6N-sulfuric acid was added to the reaction mixture, followed by extraction with diethyl ether. The ether layer was dried with anhydrous sodium sulfate, followed by distilling-off of the solvent to obtain 0.46 g of crude 4-(3-trifluoromethylheptyl)anisole

Step iii) Production of 4-(3-trifluoromethylheptyl)phenol

A mixture solution of 0.64 g of the above-prepared 4-(3-trifluoromethylheptyl)anisole in 15 ml of acetic acid and 2.8 ml of 47 %-hydrobromic acid as subjected to heat-refluxing for 13 hours After the reaction, 50 ml of ice water was added to the reaction mixture, followed by extraction with diethyl ether. The ether layer was washed three times with sodium hydrogencarbonate aqueous solution and dried with anhydrous sodium sulfate, followed by distilling-off of the solvent and further distilling under reduced pressure to obtain 0.24 g of 4-(3-trifluoromethyl)phenol (Yield: 56 %, b.p. = 140°-145° C./0.036 mmHg).

Step iv) Production of 4-decyloxybiphenyl-4'-carboxylic acid-4''-(3-trifluoromethylheptyl)phenyl ester 0.4 g of 4-decyloxybiphenyl-4'-carboxylic acid and 2 ml of thionyl chloride were subjected to heat-refluxing for 1.5 hours, followed by distilling-off of excessive thionyl chloride to obtain an acid chloride. Separately, 0.21 g of triethylenediamine was added to a solution of 0.24 g of the above-prepared 4-(3-trifluoromethylheptyl)phenol in dry tetrahydrofuran. The above mixture was added to the above acid chloride, followed by stirring for 2 hours at 50° C. To the resultant mixture, 0.04 g of 60 %-sodium hydride was added, followed by stirring for 2 hours at 70° C. After the reaction, the reaction mixture was neutralized by 3N-hydrochloric acid, followed by extraction with dichloromethane. The resultant organic layer was dried with anhydrous sodium sulfate, followed by distilling-off of the solvent and two times of purification by thin-layer chromatography (eluent: hexane/ethyl acetate = 10/1 for the first time; benzene/hexane = 4/5 for the second time). The purified product was recrystallized from a mixture solvent of 1.5 ml of ethanol and 0.2 ml of diethyl ether to obtain 0.24 g of (−)-4-decyloxybiphenyl-4'-carboxylic acid-4''-(3-trifluoromethylheptyl)phenyl ester (Yield: 44%).

OPTICAL ROTATION $[\alpha]_D^{26}$ −3.2 degrees (c=2, chloroform)

$[\alpha]_{435}^{26} - 3.3$ degrees (c=2, chloroform)

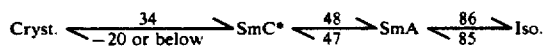

Herein, respective symbols denote the following phases, Iso.: isotropic phase, SmA: smectic A phase, SmC*: chiral smectic C phase, and Cryst.:

EXAMPLE 2

A liquid crystal composition A was prepared by mixing the following compounds in respectively indicated proportions.

| Ex. Comp. No. | Structural formula | wt. parts |
|---|---|---|
| (153) | $C_8H_{17}$—[pyrimidine]—[phenyl]—$OC_6H_{13}$ | 136 |
| (154) | $C_8H_{17}$—[pyrimidine]—[phenyl]—$OC_9H_{19}$ | 68 |
| (225) | $C_{10}H_{21}$—[pyrimidine]—[phenyl]—$OC_8H_{17}$ | 34 |
| (213) | $C_3H_7$—[H]—CO-O—[phenyl]—[pyrimidine]—$C_{11}H_{23}$ | 10.5 |
| (226) | $C_4H_9$—[H]—CO-O—[phenyl]—[pyrimidine]—$C_{11}H_{23}$ | 10.5 |
| (214) | $C_5H_{11}$—[H]—CO-O—[phenyl]—[pyrimidine]—$C_{11}H_{23}$ | 21 |

The liquid crystal composition A was further mixed with the following Example Compound No. I-62 in the proportions indicated below to provide a liquid crystal composition B.

| Ex. Comp. No. | Structural formula | wt. parts |
|---|---|---|
| (I-62) | $C_{10}H_{21}O$—[phenyl]—[phenyl]—CO-O—[phenyl]—$(CH_2)_2\overset{*}{C}HC_4H_9$ with $CF_3$ | 5 |
| | Composition A | 95 |

Two 0.7 mm-thick glass plates were provided and respectively coated with an ITO film to form an electrode for voltage application, which was further coated with an insulating layer of vapor-deposited $SiO_2$. On the insulating layer, a 0.2%-solution of silane coupling agent (KBM-602, available from Shinetsu Kagaku K. K.) in isopropyl alcohol was applied by spinner coating at a speed of 2000 rpm for 15 second and subjected to hot curing treatment at 120° C. for 20 min.

Further, each glass plate provided with an ITO film and treated in the above described manner was coated with a 1.5%-solution of polyimide resin precursor (SP-510, available from Toray K. K.) in dimethylacetoamide by a spinner coater rotating at 2000 rpm for 15 seconds. Thereafter, the coating film was subjected to heat curing at 300° C. for 60 min. to obtain about 250 Å-thick film. The coating film was rubbed with acetate fiber-planted cloth. The thus treated two glass plates were washed with isopropyl alcohol. After alumina beads with an average particle size of 2.0 microns were dispersed on one of the glass plates, the two glass plates were applied to each other with a bonding sealing agent (Lixon Bond, available from Chisso K. K.) so that their rubbed directions were parallel to each other and heated at 100° C. for 60 min. to form a blank cell. The cell gap was found to be about 2 microns as measured by a Berek compensator.

Then, the liquid crystal composition B was heated into an isotropic liquid, and injected into the above prepared cell under vacuum and, after sealing, was gradually cooled at a rate of 20° C./hour to 25° C. to prepare a ferroelectric liquid crystal device.

The ferroelectric liquid crystal device was subjected to measurement of the magnitude of spontaneous polarization Ps and an optical response time (time from voltage application until the transmittance change reaches 90% of the maximum under the application of a peak-to-peak voltage Vpp of 20 V in combination with right-angle cross-nicol polarizers).

The results are shown in Table 1 below.

TABLE 1

| Temperature (°C.) | 45 | 30 | 10 |
|---|---|---|---|
| Response time (μsec) | 40 | 75 | 200 |
| Ps (nC/cm²) | 1.0 | 1.3 | 1.7 |

EXAMPLE 3

A blank cell was prepared in the same manner as in Example 2 by using a 2% aqueous solution of polyvinyl alcohol resin (PVA-117, available from Kuraray K. K.) instead of the 1.5%-solution of polyimide resin precursor in dimethylacetoamide on each electrode plate. A ferroelectric liquid crystal device was prepared by filling the blank cell with the liquid crystal composition B prepared in Example 2. The liquid crystal device was subjected to measurement of optical response time in the same manner as in Example 2. The results are shown below.

| | 45° C. | 30° C. | 10° C. |
|---|---|---|---|
| Response time (μsec) | 38 | 71 | 198 |

EXAMPLE 4

A blank cell was prepared in the same manner as in Example 2 except for omitting the SiO₂ layer to form an alignment control layer composed of the polyimide resin layer alone on each electrode plate. A ferroelectric liquid crystal device was prepared by filling the blank cell with the liquid crystal composition B prepared in Example 2. The liquid crystal device was subjected to measurement of optical response time in the same manner as in Example 2. The results are shown below.

| | 45° C. | 30° C. | 10° C. |
|---|---|---|---|
| Response time (μsec) | 36 | 67 | 192 |

As is apparent from the above Examples 3 and 4, also in the cases of different device structures, the devices containing the ferroelectric liquid crystal composition B according to the present invention respectively provided remarkably improved high-speed responsiveness.

EXAMPLE 5

4-octyloxybiphenyl-4'-carboxylic acid-4''-(3-trifluoromethylheptyl)phenyl ester (Example Compound No. I-82) was synthesized through the following reaction scheme.

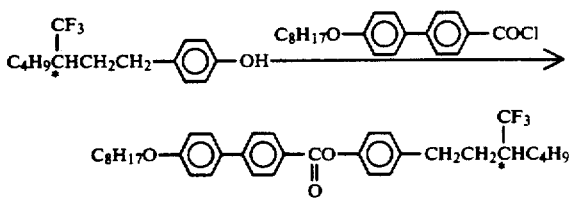

4-octyloxybiphenyl-4'-carboxylic acid-4''-(3-trifluoromethylheptyl)phenyl ester was prepared in the same manner as in Example 1 except that (−)-3-trifluoromethylheptanoic acid was used instead of (+)-3-trifluoromethylheptanoic acid in Step i) of Example 1 and that 4-octyloxybiphenyl-4'-carboxylic acid was used instead of 4-decyloxybiphenyl-4'-carboxylic acid in Step iv) of Example 1.

EXAMPLE 6

4-(5'-heptyl-2'-pyrimidinyl)benzoic acid-4''-(3-trifluoromethylheptyl)phenyl ester (Example Compound No. I-83) was synthesized through the following reaction scheme.

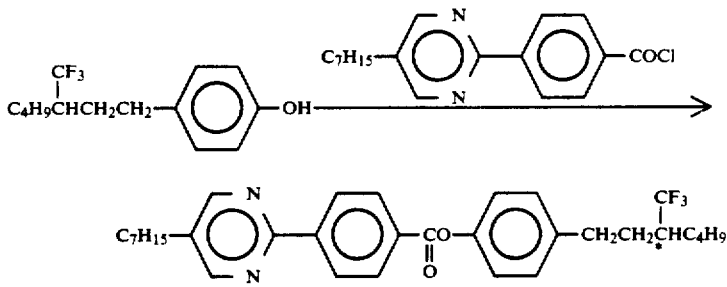

4-(5'-heptyl-2'-pyrimidinyl)benzoic acid-4''-(3-trifluoromethylheptyl)phenyl ester was prepared in the same manner as in Example 1 except that (−)-3-trifluoromethylheptanoic acid was used instead of (+)-3-trifluoromethylheptanoic acid in Step i) of Example 1 and that 4-(5'-heptyl-2'-pyrimidinyl)benzoic acid was used instead of 4-decyloxybiphenyl-4'-carboxylic acid in Step iv) of Example 1.

OPTICAL ROTATION $[\alpha]_D^{28} + 2.43$ degrees, $[\alpha]_{435}^{27} + 3.95$ degrees (C=3.04, CHCl₃)

EXAMPLE 7

4-(4'-octylcyclohexyl)benzoic acid-4''-(3-trifluoromethylheptyl)phenyl ester (Example Compound No. I-84) was synthesized through the following reaction scheme.

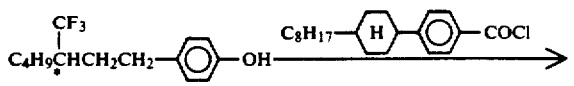

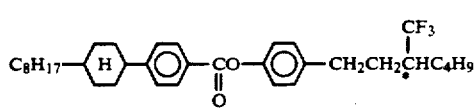

4-(4'-octylcyclohexyl)benzoic acid-4'''-(3-trifluoromethylheptyl)phenyl ester was prepared in the same manner as in Example 1 except that (−)-3-trifluoromethylheptanoic trifluoromethylheptanoic acid was used instead of (+)- 3-trifluoromethylheptanoic acid in Step i) of Example 1 and that 4-(4'-octylcyclohexyl)benzoic acid was used instead of 4-decyloxybiphenyl-4'-carboxylic acid in Step iv) of Example 1.

OPTICAL ROTATION $[\alpha]_D^{28.5} + 2.17$ degrees, $[\alpha]_{435}^{27.5} + 3.49$ degrees (C = 2.12, CHCl$_3$)

EXAMPLE 8

4-decyloxy-4'-biphenylcarboxylic acid-4''-(3-trifluoromethylnonyl)phenyl ester (Example Compound No. I-85) was synthesized through the following reaction 4-decyloxy-4'-biphenylcarboxylic acid-4''-(3-trifluoromethylnonyl)phenyl ester was prepared in the same manner as in Example 1 except that (−)-3-trifluoromethylnonanoic acid was used instead of (+)-3trifluoromethylheptanoic acid in Step i) of Example 1.

OPTICAL ROTATION $[\alpha]_D^{27} + 1.3$ degrees, $[\alpha]_{435}^{26.6} + 2.8$ degrees (C = 1.06, CHCl$_3$)

EXAMPLE 9

4-dodecyloxy-4'-biphenylcarboxylic acid-4''-(3-trifluoromethylnonyl)phenyl ester (Example Compound No. I-86) was synthesized through the following reaction scheme.

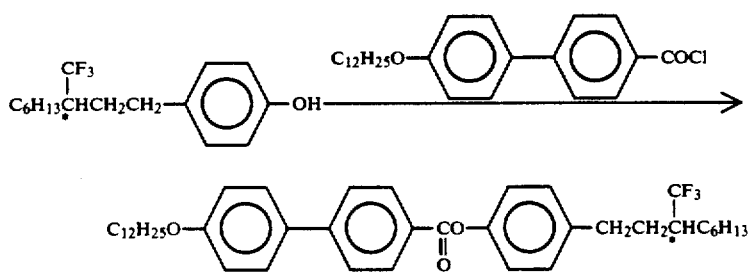

4-dodecyloxy-4'-biphenylcarboxylic acid-4''-(3-trifluoromethylnonyl)phenyl ester was prepared in the same manner as in Example 8 except that 4-dodecyloxy-4'-biphenylcarboxylic acid was used instead of 4-decyloxy-4'-biphenylcarboxylic acid in Example 8.

OPTICAL ROTATION $[\alpha]_D + 1.5$ degrees, $[\alpha]_{435}^{25} + 3.4$ degrees (C = 1.002, CHCl$_3$)

EXAMPLE 10

4-octyloxy-4'-biphenylcarboxylic acid-4''-(3-trifluoromethylnonyl)phenyl ester (Example Compound No. I-87) was synthesized through the following reaction

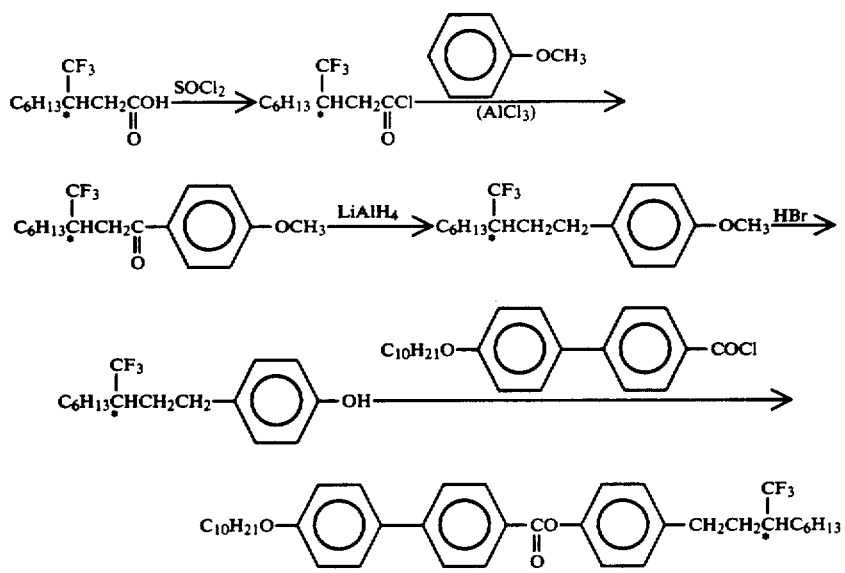

4-decyloxy-4'-biphenylcarboxylic acid-4''-(3-trifluoromethylnonyl)phenyl ester was prepared in the tion scheme.

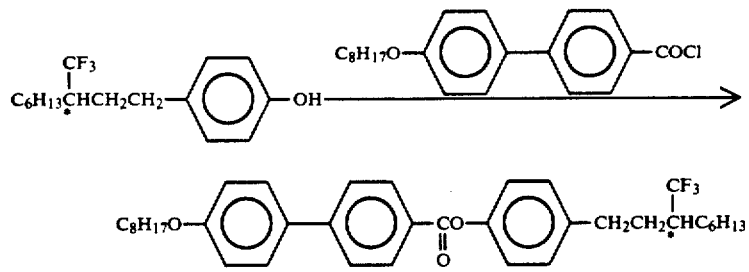

4-octyloxy-4'-biphenylcarboxylic acid-4''-(3-trifluoromethylnonyl)phenyl ester was prepared in the same manner as in Example 8 except that 4-octyloxy-4'-biphenylcarboxylic acid was used instead of 4-decyloxy-4'-biphenylcarboxylic acid in Example 8.

OPTICAL ROTATION $[\alpha]_D^{20} + 1.7$ degrees, $[\alpha]_{435}^{21} + 3.3$ degrees (C = 1.029, CHCl$_3$)

The mesomorphic compounds prepared in Examples 5–10 respectively showed the phase transition series indicated in Table 2 below.

TABLE 2

| Example No. | Structural formula | Phase transition temperature (°C.) |
|---|---|---|
| 5 | $C_8H_{17}O$-〇-〇-CO-O-〇-$CH_2CH_2\overset{*}{C}H C_4H_9$ (with $CF_3$) | Cryst. $\underset{17}{\overset{49}{\rightleftarrows}}$ SmC* $\underset{20}{\overset{}{\rightleftarrows}}$ SmA $\underset{89}{\overset{86}{\rightleftarrows}}$ Iso. |
| 6 | $C_7H_{15}$-(pyridine)-〇-CO-O-〇-$CH_2CH_2\overset{*}{C}H C_4H_9$ (with $CF_3$) | Cryst. $\underset{69}{\overset{94}{\rightleftarrows}}$ Sm3 $\underset{117}{\overset{119}{\rightleftarrows}}$ SmA $\underset{117}{\overset{119}{\rightleftarrows}}$ Iso. |
| 7 | $C_8H_{17}$-(cyclohexyl H)-〇-CO-O-〇-$CH_2CH_2\overset{*}{C}H C_4H_9$ (with $CF_3$) | Cryst. $\underset{5}{\overset{48}{\rightleftarrows}}$ Sm3 $\underset{61}{\overset{62}{\rightleftarrows}}$ SmA $\underset{85}{\overset{87}{\rightleftarrows}}$ Iso. |
| 8 | $C_{10}H_{21}O$-〇-〇-CO-O-〇-$CH_2CH_2\overset{*}{C}H C_6H_{13}$ (with $CF_3$) | Cryst. $\underset{10}{\overset{45}{\rightleftarrows}}$ SmC* $\underset{38}{\overset{90}{\rightleftarrows}}$ SmA $\underset{120}{\overset{121}{\rightleftarrows}}$ Iso. |
| 9 | $C_{12}H_{25}O$-〇-〇-CO-O-〇-$CH_2CH_2\overset{*}{C}H C_6H_{13}$ (with $CF_3$) | Cryst. $\underset{37}{\overset{65}{\rightleftarrows}}$ SmC* $\underset{94}{\overset{95}{\rightleftarrows}}$ SmA $\underset{115}{\overset{116}{\rightleftarrows}}$ Iso. |
| 10 | $C_8H_{17}O$-〇-〇-CO-O-〇-$CH_2CH_2\overset{*}{C}H C_6H_{13}$ (with $CF_3$) | Cryst. $\underset{19}{\overset{21}{\rightleftarrows}}$ Sm4 $\underset{55}{\overset{53}{\rightleftarrows}}$ Sm3 $\underset{62}{\overset{62}{\rightleftarrows}}$ SmC* $\underset{79}{\overset{79}{\rightleftarrows}}$ SmA $\underset{129}{\overset{130}{\rightleftarrows}}$ Iso. |

Sm3, Sm4: smectic phase other than smectic A phase and smectic C phase (un-identified)

EXAMPLE 11

Production of 4-dodecyloxybiphenyl-4'-carboxylic acid-4"-(3-trifluoromethylheptyl)phenyl ester (Example Compound No. I-88)

4-dodecyloxybiphenyl-4'-carboxylic acid-4"-(3-trifluoromethylheptyl)phenyl ester was prepared in the same manner as in Example 1 except that 4-dodecyloxybiphenyl-4'-carboxylic acid was used instead of 4-decyloxybiphenyl-4'-carboxylic acid in Step iv) of Example 1.

OPTICAL ROTATION $[\alpha]_D^{26}$ + 1.6 degrees, $[\alpha]_{435}^{28}$ + 2.8 degrees (C = 3.30, CHCl$_3$)

EXAMPLE 12

Production of 4-hexadecyloxybiphenyl-4'-carboxylic acid-4"-(3-trifluoromethylheptyl)phenyl ester (Example Compound No. I-89).

4-hexadecyloxybiphenyl-4'-carboxylic acid-4"(3-trifluoromethylheptyl)phenyl ester was prepared in the same manner as in Example 1 except that 4-hexadecyloxybiphenyl-4'-carboxylic acid was used instead of 4-decyloxybiphenyl-4'-carboxylic acid in Step iv) of Example 1.

OPTICAL ROTATION $[\alpha]_D^{20}$ − 1.2 degrees, $[\alpha]_{435}^{23}$ − 2.2 degrees (C = 3.34, CHCl$_3$)

EXAMPLE 13

Production of 4-hexyloxybiphenyl-4'-carboxylic acid-4"-(3-trifluoromethylheptyl)phenyl ester (Example Compound No. I-90)

4-hexyloxybiphenyl-4'-carboxylic acid-4"-(3-trifluoromethylheptyl)phenyl ester was prepared in the same manner as in Example 1 except that 4-hexyloxybiphenyl-4'-carboxylic acid was used instead of 4-decyloxybiphenyl-4'-carboxylic acid in Step iv) of Example 1.

OPTICAL ROTATION $[\alpha]_D^{27}$ − 2.4 degrees, $[\alpha]_{435}^{27}$ − 3.8 degrees (C = 2.53, CHCl$_3$)

EXAMPLE 14

Production of 4-heptylbiphenyl-4'-carboxylic acid-4"-(3-trifluoromethylheptyl)phenyl ester (Example Compound No. I-91)

4-heptylbiphenyl-4'-carboxylic acid-4"-(3-trifluoromethylheptyl)phenyl ester was prepared in the same manner as in Example 1 except that 4-heptylbiphenyl-4'-carboxylic acid was used instead of 4-decyloxybiphenyl-4'-carboxylic acid in Step iv) of Example 1.

OPTICAL ROTATION $[\alpha]_D^{25}$ − 2.1 degrees, $[\alpha]_{435}^{25}$ − 3.4 degrees (C = 2.33, CHCl$_3$)

EXAMPLE 15

Production of 4-hexadecyloxybiphenyl-4'-carboxylic acid-4"-(3-trifluoromethylnonyl)phenyl ester (Example Compound No. I-92)

4-hexadecyloxybiphenyl-4'-carboxylic acid-4"-(3-trifluoromethylnonyl)phenyl ester was prepared in the same manner as in Example 8 except that 4-hexadecyloxybiphenyl-4'-carboxylic acid was used instead of 4-decyloxybiphenyl-4'-carboxylic acid in Example 8.

EXAMPLE 16

Production of 4-heptylbiphenyl-4'-carboxylic acid-4"-(3-trifluorommethylnonyl)phenyl ester (Example Compound No. I-93)

4-heptylbiphenyl-4'-carboxylic acid-4"-(3-trifluoromethylnonyl)phenyl ester was prepared in the same manner as in Example 8 except that 4-heptylbiphenyl-4'-carboxylic acid was used instead of 4-decyloxybiphenyl-4'-carboxylic acid in Example 8.

EXAMPLE 17

Production of 4-(5'-heptyl-2'-pyrimidinyl)benzoic acid-4"-(3-trifluoromethylnonyl)phenyl ester (Example Compound No. I-94)

4-(5'-heptyl-2'-pyrimidinyl)benzoic acid-4"-(3-trifluoromethylnonyl)phenyl ester was prepared in the same manner as in Example 8 except that 4-(5'-heptyl-2'-pyrimidinyl)benzoic acid was used instead of 4-decyloxybiphenyl-4'-carboxylic acid in Example 8.

OPTICAL ROTATION $[\alpha]_D^{27}$ + 1.49 degrees, $[\alpha]_{435}^{25}$ + 4.98 degrees (C = 1.0, CHCl$_3$)

EXAMPLE 18

Production of 4-(4'-octylcyclohexyl)benzoic acid-4"-(3-trifluoromethylnonyl)phenyl ester (Example Compound No. I-95)

4-(4'-octylcyclohexyl)benzoic acid-4"-(3-trifluoromethylnonyl)phenyl ester was prepared in the same manner as in Example 8 except that 4-(4'-octylcyclohexyl)benzoic acid was used instead of 4-decyloxybiphenyl-4'-carboxylic acid in Example 8.

OPTICAL ROTATION $[\alpha]_{435}^{25}$ + 4.71 degrees (C = 0.85, CHCl$_3$)

EXAMPLE 19

Production of 4-hexyloxybiphenyl-4'-carboxylic acid-4"-(3-trifluoromethylnonyl)phenyl ester (Example Compound No. I-96)

4-hexyloxybiphenyl-4'-carboxylic acid-4"-(3-trifluoromethylnonyl)phenyl ester was prepared in the same manner as in Example 8 except that 4-hexyloxybiphenyl-4'-carboxylic acid was used instead of 4-decyloxybiphenyl-4'-carboxylic acid in Example 8.

OPTICAL ROTATION $[\alpha]_D^{26}$ + 2.96 degrees, $[\alpha]_{435}^{25}$ + 7.9 degrees (C = 0.81, CHCl$_3$)

The mesomorphic compounds prepared in Examples 11-19 respectively showed the phase transition series indicated in Table 3 below.

TABLE 3

| Example No. | Structural formula | Phase transition temperature (°C.) |
|---|---|---|
| 11 | C₁₂H₂₅O–⬡–⬡–COO–⬡–CH₂CH₂*CH(CF₃)C₄H₉ | Unmeasured |
| 12 | C₁₆H₃₃O–⬡–⬡–COO–⬡–CH₂CH₂*CH(CF₃)C₄H₉ | Cryst. ⇌(47/25) SmA ⇌(75/74) Iso.; SmA ⇌(35/25) SmC* |
| 13 | C₆H₁₃O–⬡–⬡–COO–⬡–CH₂CH₂*CH(CF₃)C₄H₉ | Cryst. ⇌(75/52) SmA ⇌(103/103) Iso. |
| 14 | C₇H₁₅–⬡–⬡–COO–⬡–CH₂CH₂*CH(CF₃)C₄H₉ | Cryst. ⇌(55/<20) SmA ⇌(117/115) Iso. |
| 15 | C₁₆H₃₃O–⬡–⬡–COO–⬡–CH₂CH₂*CH(CF₃)C₆H₁₃ | Cryst. ⇌(42/22) SmA ⇌(52/50) Iso. |
| 16 | C₇H₁₅–⬡–⬡–COO–⬡–CH₂CH₂*CH(CF₃)C₆H₁₃ | Cryst. ⇌(53/<−50) Sm3 ⇌(67/67) SmA ⇌(104/104) Iso.; Sm3 ⇌25 Sm4 |
| 17 | C₇H₁₅–(pyrimidine)–⬡–COO–⬡–CH₂CH₂*CH(CF₃)C₆H₁₃ | Cryst. ⇌(71/58) Sm ⇌(103/103) Iso. |
| 18 | C₈H₁₇–(cyclohexyl)–⬡–COO–⬡–CH₂CH₂*CH(CF₃)C₆H₁₃ | Cryst. ⇌(43/5) SmA ⇌(65/64) Iso.; SmA ⇌43 Sm3 |

TABLE 3-continued
| Example No. | Structural formula | Phase transition temperature (°C.) |
|---|---|---|
| 19 |  | Cryst. ⇌ 72/49 SmA ⇌ 90/90 Iso. |
Sm: smectic phase (un-identified)

As described hereinabove, according to the present invention, there are provided a mesomorphic compound, a liquid crystal composition containing the compound, and a liquid crystal device using the composition which shows a good switching characteristic, an improved low-temperature operation characteristic and decreased high-speed responsiveness when the composition assumes a chiral smectic phase. According to the present invention, there is further provided a display apparatus utilizing the liquid crystal device of the present invention as a display unit, which shows good display characteristics in combination of a light source, a drive circuit, etc.

What is claimed is:

1. A mesomorphic compound represented by the following formula (I):

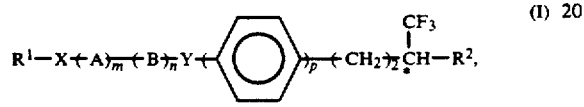

wherein $R^1$ denotes an alkyl group having 1–18 carbon atoms; $R^2$ denotes an alkyl group having 1–12 carbon atoms; A and B respectively denote

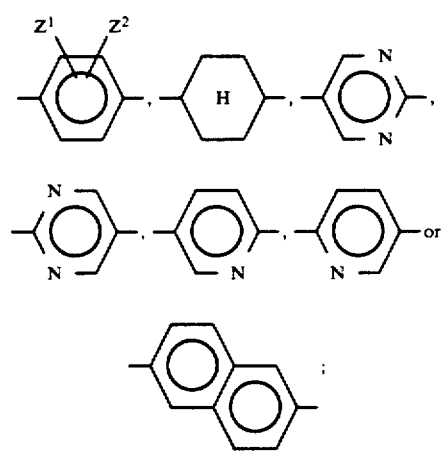

$Z^1$ and $Z^2$ respectively denote —H, —CH$_3$, —OCH$_3$, —CN or halogen; m and n respectively denote 0, 1 or 2 and p denotes 1 or 2 with proviso that $m+n+p=2$ or 3; X denotes a single bond,

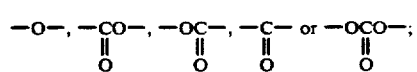

Y denotes a single bond 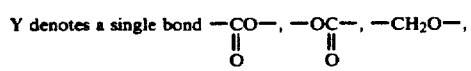

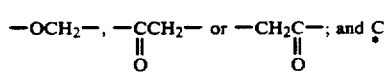

denotes an asymmetric carbon atom.

2. A mesomorphic compound according to claim 1, which is represented by any one of the following formulas (a)–(z):

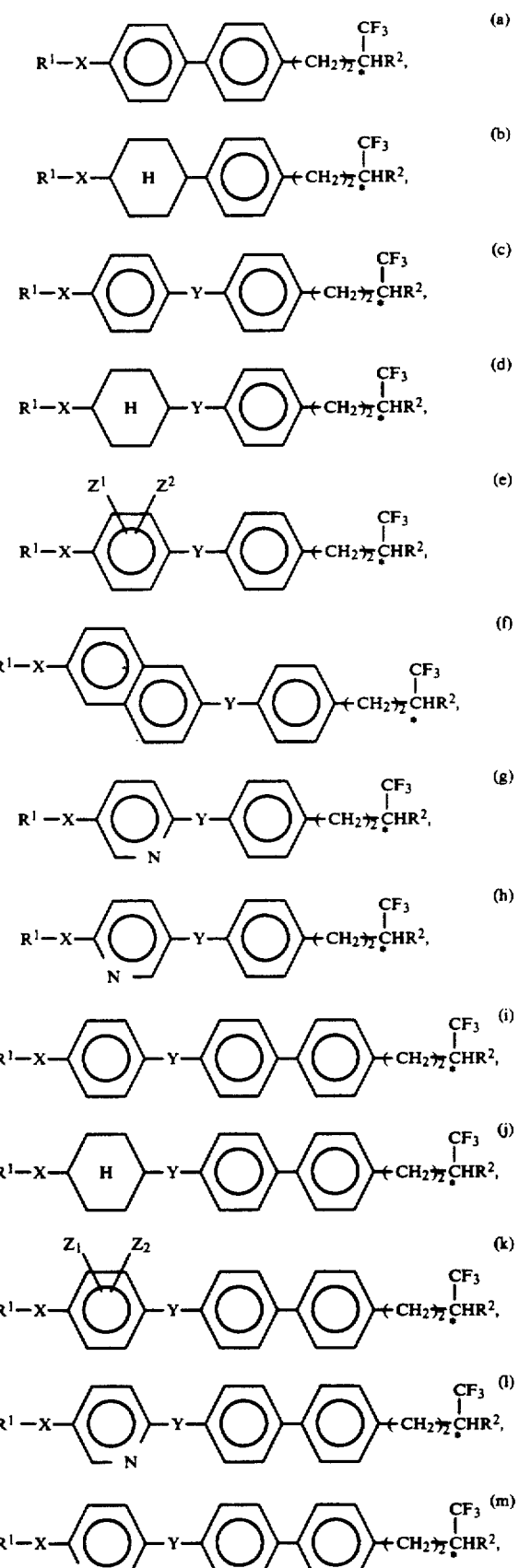

-continued

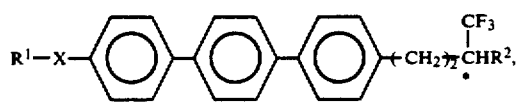 (n)

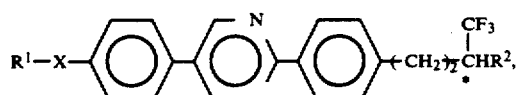 (o)

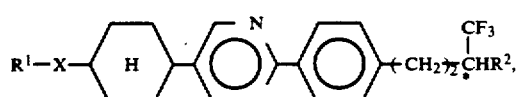 (p)

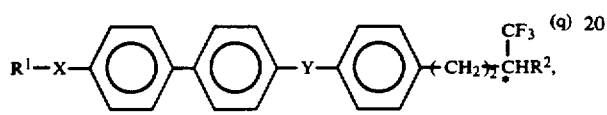 (q)

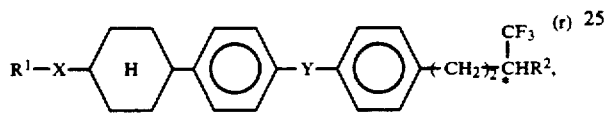 (r)

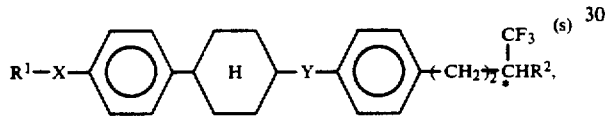 (s)

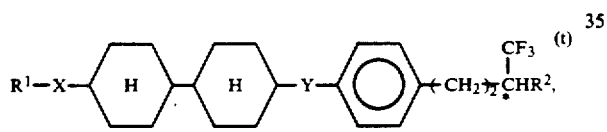 (t)

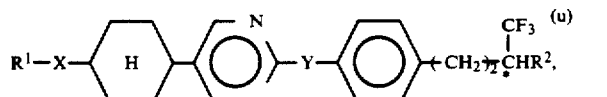 (u)

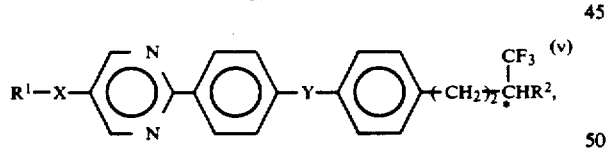 (v)

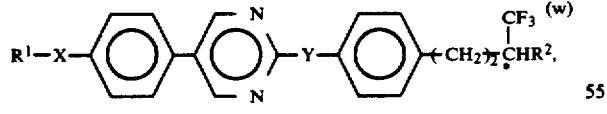 (w)

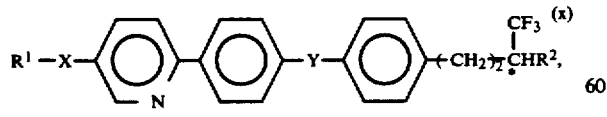 (x)

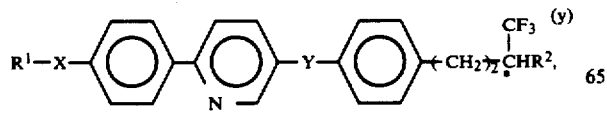 (y)

and

-continued

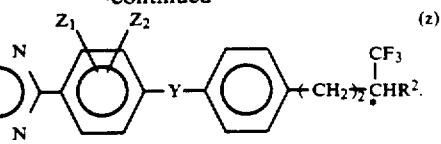 (z)

3. A mesomorphic compound according to claim 1, which assumes a chiral smectic phase.

4. A liquid crystal composition comprising at least two mesomorphic compounds, at least one of which is a mesomorphic compound of the formula (I) according to claim 1.

5. A liquid crystal composition according to claim 4, wherein said mesomorphic compound of the formula (I) is represented by any one of the following formulas (a)-(z):

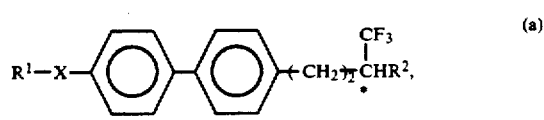 (a)

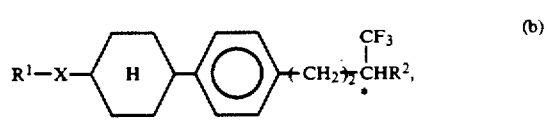 (b)

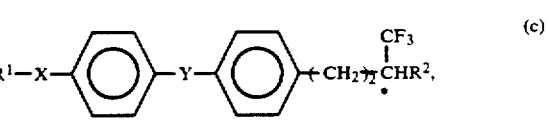 (c)

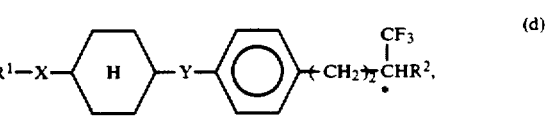 (d)

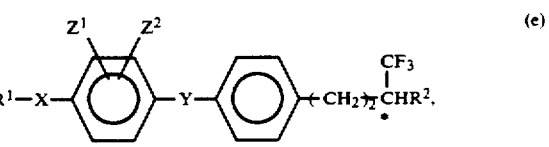 (e)

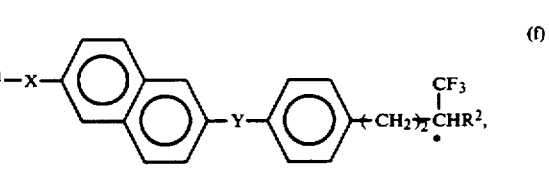 (f)

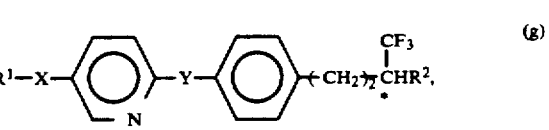 (g)

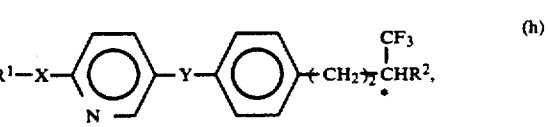 (h)

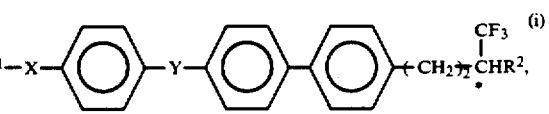 (i)

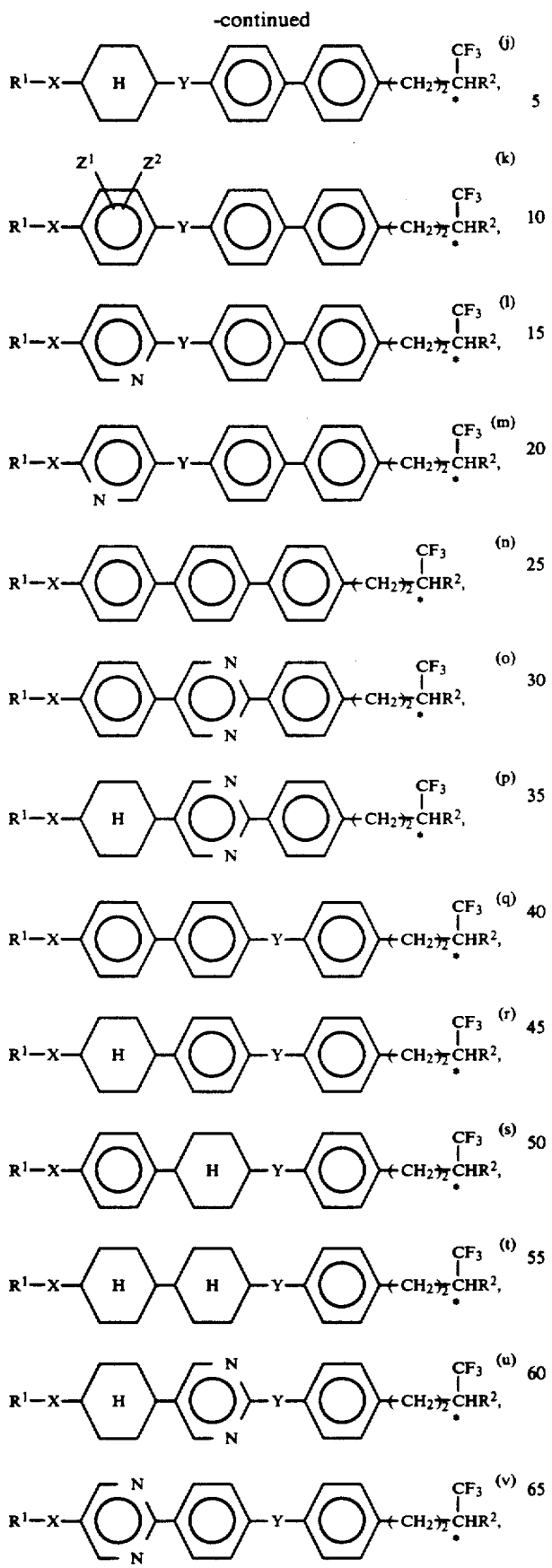

6. A liquid crystal composition according to claim 4, which comprises 1-500 wt. parts of a mesomorphic compound of the formula (I) per 100 wt. parts of at least one species of another mesomorphic compound other than the mesomorphic compound of the formula (I).

7. A liquid crystal composition according to claim 4, which comprises 1-500 wt. parts of two or more species of mesomorphic compounds of the formula (I) per 100 wt. parts of at least one species of another mesomorphic compound other than the mesomorphic compound of the formula (I).

8. A liquid crystal composition according to claim 4, which assumes a chiral smectic phase.

9. A liquid crystal device, comprising a pair of electrode plates and a liquid crystal composition according to claim 4 disposed between the electrode plates.

10. A liquid crystal device according to claim 9, which further comprises an insulating alignment control layer.

11. A display apparatus comprising a liquid crystal device according to claim 9, and voltage application means for driving the liquid crystal device.

12. A display apparatus according to claim 11, wherein the liquid crystal device constitutes a display panel wherein the alignment direction of liquid crystal molecules is switched by utilizing ferroelectricity of the liquid crystal composition to effect display.

13. A display apparatus according to claim 12, which further comprises a light source.

14. A display method comprising:
providing a liquid crystal composition according to claim 4 having ferroelectricity, and
switching the alignment direction of liquid crystal molecules based on the ferroelectricity of the liquid crystal composition to effect display.

15. A display method, comprising:
providing a liquid crystal device according to claim 9, and
switching the alignment direction of liquid crystal molecules to effect display based on the ferroelectricity of the liquid crystal composition contained in the liquid crystal device.

* * * * *

UNITED STATES PATENT AND TRADEMARK OFFICE
CERTIFICATE OF CORRECTION

PATENT NO. : 5,217,644
DATED : June 8, 1993
INVENTOR(S) : HIROYUKI NOHIRA, ET AL.

Page 1 of 4

It is certified that error appears in the above-identified patent and that said Letters Patent is hereby corrected as shown below:

IN [57] ABSTRACT

Line 3, "analkyl" should read --an alkyl--.
Line 6, "'$CH_3$," should read -- —$CH_3$,--.

COLUMN 2

Line 57, "t" should read --to--.

COLUMN 3

Line 3, "larization" should read --larization.--.

COLUMN 6

Line 60, "C" should read --$\underset{*}{C}$--.

COLUMN 27

Formula (16), "$C_{12}H_{25}O$" should read --$C_{12}H_{25}$--.

COLUMN 31

Formula (39), "$\begin{array}{c} CH_3 \\ | \\ OCH_2\underset{*}{C}H_2H_5 \end{array}$" should read --$\begin{array}{c} CH_3 \\ | \\ OCH_2\underset{*}{C}HC_2H_5 \end{array}$--.

Formula (40), "$C_8H_{17}$—⌬—" should read --$C_8H_{17}$—⌬H—--.

UNITED STATES PATENT AND TRADEMARK OFFICE
CERTIFICATE OF CORRECTION

PATENT NO. : 5,217,644
DATED : June 8, 1993
INVENTOR(S) : HIROYUKI NOHIRA, ET AL.

It is certified that error appears in the above-identified patent and that said Letters Patent is hereby corrected as shown below:

COLUMN 31

Formula (47), 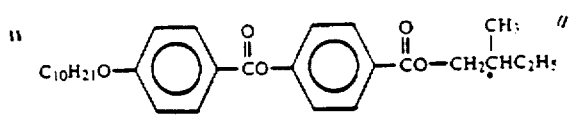

should read

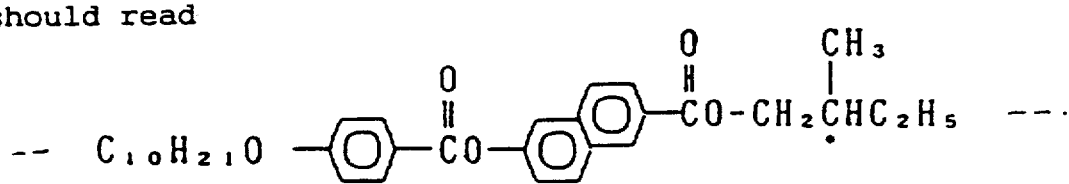

COLUMN 33

Formula (54), 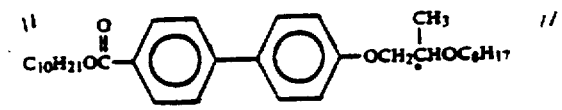

should read

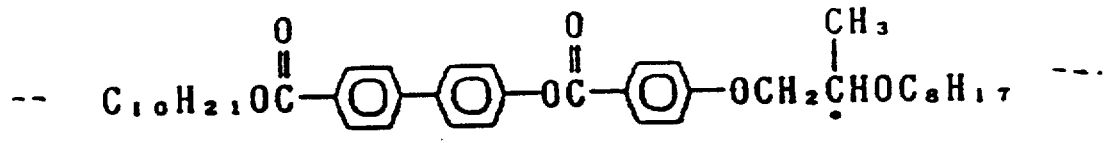

UNITED STATES PATENT AND TRADEMARK OFFICE
CERTIFICATE OF CORRECTION

PATENT NO. : 5,217,644
DATED : June 8, 1993
INVENTOR(S) : HIROYUKI NOHIRA, ET AL.

It is certified that error appears in the above-identified patent and that said Letters Patent is hereby corrected as shown below:

COLUMN 39

Formula (97), should read

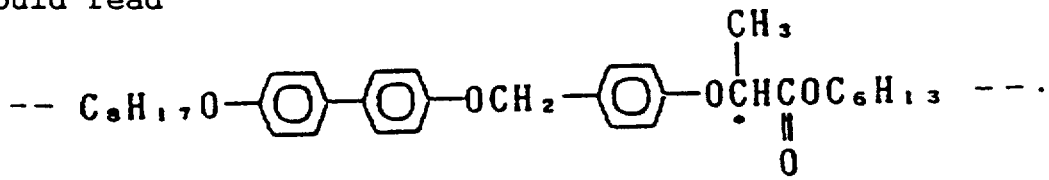

COLUMN 57

Formula (209), "$C_{10}H_{21}$" should read --$C_{10}H_{21}O$--.

COLUMN 63

Line 37, "$(P_1)$ 24" should read --$(P\perp)$ 24--.
Line 47, "$(P_1)$ 24" should read --$(P\perp)$ 24--.
Line 54, "i e.," should read --i.e.,--.
Line 59, "voltage" should read --voltage.--.
Line 63, "eve" should read --even--.

COLUMN 65

Step ii), "$CH_3$" should read --$CF_3$--.

Line 33, "4 5 ml" should read --4.5 ml--.
Line 68, "hours" should read --hours.--.

UNITED STATES PATENT AND TRADEMARK OFFICE
CERTIFICATE OF CORRECTION

PATENT NO. : 5,217,644
DATED : June 8, 1993
INVENTOR(S) : HIROYUKI NOHIRA, ET AL.

It is certified that error appears in the above-identified patent and that said Letters Patent is hereby corrected as shown below:

COLUMN 67

Line 2, insert: --Phase Transition Temperature (C°)--.
Line 8, "Cryst.:" should read --Cryst.: crystal.--.
Line 49, "i" should read --in--.

COLUMN 68

Line 1, "second" should read --seconds--.

COLUMN 71

Line 14, "trifluoromethylheptanoic" should be deleted.
Line 41, "tion" should read --tion scheme.--.

COLUMN 78

Line 14, "-(3-trifluorommethylnonyl)phenyl" should read
-- -(3-trifluoromethylnonyl)phenyl--.

Signed and Sealed this

Sixteenth Day of May, 1995

Attest:

BRUCE LEHMAN

Attesting Officer    Commissioner of Patents and Trademarks